(12) United States Patent
Chen et al.

(10) Patent No.: US 8,030,503 B2
(45) Date of Patent: Oct. 4, 2011

(54) PROCESS FOR THE PREPARATION OF EPOTHILONES

(75) Inventors: Yue Chen, Hayward, CA (US); Yong Li, Palo Alto, CA (US)

(73) Assignee: Kosan Biosciences Incorporated, Princeton, NJ (US)

( * ) Notice: Subject to any disclaimer, the term of this patent is extended or adjusted under 35 U.S.C. 154(b) by 678 days.

(21) Appl. No.: 12/117,876

(22) Filed: May 9, 2008

(65) Prior Publication Data

US 2008/0319211 A1 Dec. 25, 2008

Related U.S. Application Data

(60) Provisional application No. 60/917,572, filed on May 11, 2007.

(51) Int. Cl.
*C07D 309/30* (2006.01)

(52) U.S. Cl. .................................................. 549/292
(58) Field of Classification Search ................... 549/292
See application file for complete search history.

(56) References Cited

U.S. PATENT DOCUMENTS

| 5,527,805 A | 6/1996 | Smith et al. |
| 6,380,400 B1 | 4/2002 | Fedij et al. |
| 2003/0045711 A1 | 3/2003 | Ashley et al. |
| 2004/0152708 A1 | 8/2004 | Li et al. |
| 2005/0043376 A1 | 2/2005 | Danishefsky et al. |
| 2007/0078140 A1 | 4/2007 | Borzilleri et al. |

OTHER PUBLICATIONS

International Search Report and Written Opinion of International Application No. PCT/US08/63173.

*Primary Examiner* — Andrew D Kosar
(74) *Attorney, Agent, or Firm* — Hong Liu; Fox Rothschild LLP

(57) ABSTRACT

Intermediates in the preparation of epothilones and epothilone analogs are provided along with synthetic methods useful in the synthesis of epothilone compounds.

23 Claims, 7 Drawing Sheets

Reagents: (a) KO$^t$Bu, MeI, DMF, 60 °C; (b) diisobutylaluminum hydride, CH$_2$Cl$_2$, -78 °C; (c) 1,3-propanedithiol, BF$_3$·OEt$_2$, CH$_3$NO$_2$, -20 °C; (d) $^t$butyldimethylsilyl triflate, 2,6-lutidine, CH$_2$Cl$_2$; (e) [bis(trifluoroacetoxy)]iodobenzene, CH$_3$CN, H$_2$O; (f) (N-acetyl)-(2R)-bornane-10,2-sultam, dibutylboron triflate, diisopropylethylamine, CH$_2$Cl$_2$, -78 °C; (g) $^t$butyldimethylsilyl triflate, 2,6-lutidine, CH$_2$Cl$_2$; (h) LiOH, H$_2$O$_2$, tetrahydrofuran.

FIGURE 3

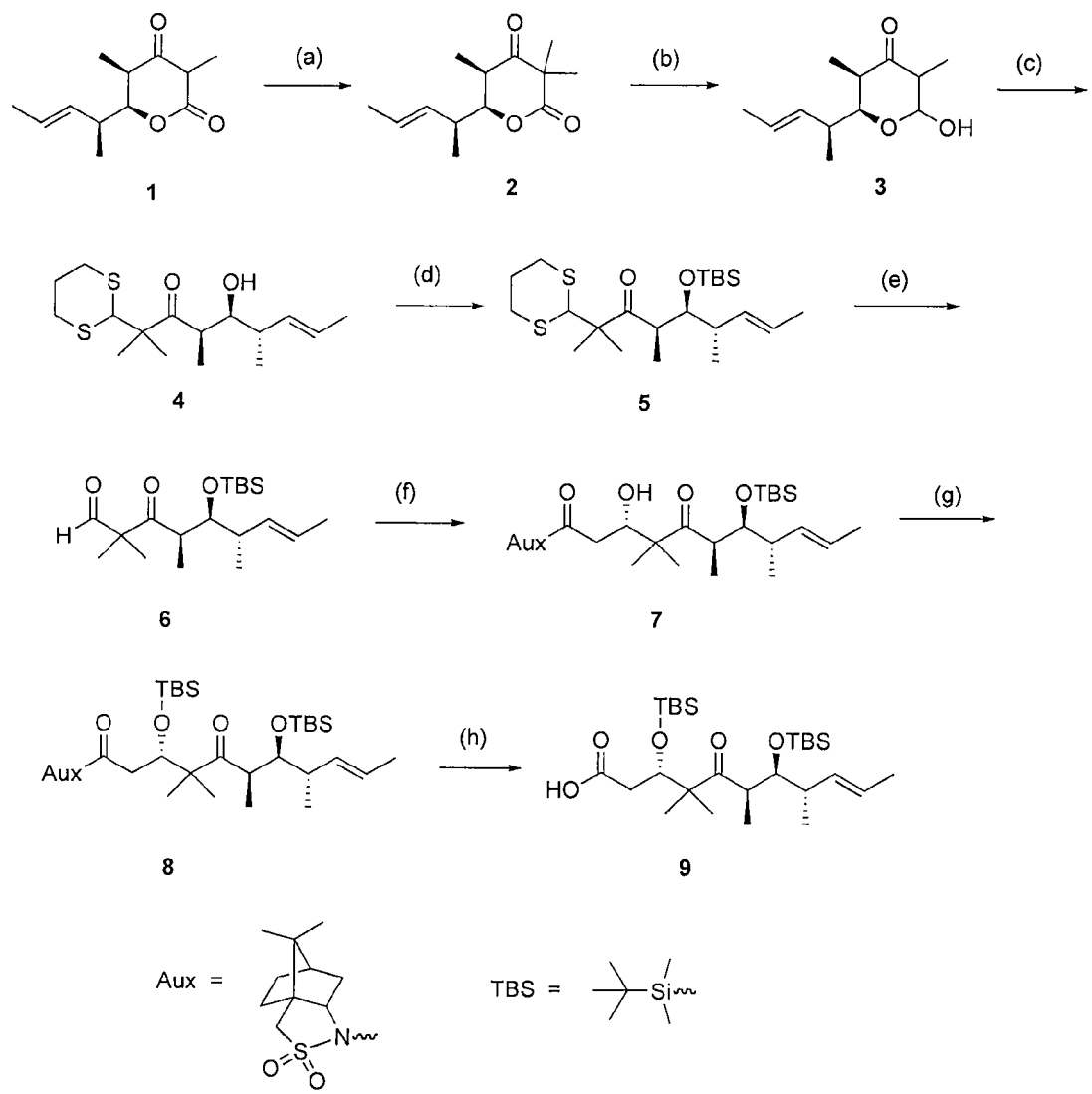

Reagents: (a) KO$^t$Bu, MeI, DMF, 60 °C; (b) diisobutylaluminum hydride, CH$_2$Cl$_2$, -78 °C; (c) 1,3-propanedithiol, BF$_3$•OEt$_2$, CH$_3$NO$_2$, -20 °C; (d) $^t$butyldimethylsilyl triflate, 2.6-lutidine, CH$_2$Cl$_2$; (e) [bis(trifluoroacetoxy)]iodobenzene, CH$_3$CN, H$_2$O; (f) (N-acetyl)-(2R)-bornane-10,2-sultam, dibutylboron triflate, diisopropylethylamine, CH$_2$Cl$_2$, -78 °C; (g) $^t$butyldimethylsilyl triflate, 2.6-lutidine, CH$_2$Cl$_2$; (h) LiOH, H$_2$O$_2$, tetrahydrofuran.

Reagents: (a) 1-(3-dimethylaminpropyl)-3-ethylcarbodiimide•HCl, 4-(dimethylamino)pyridine, CH$_2$Cl$_2$; (b) (1,3-Bis-(2,4,6-trimethylphenyl)-2,3-dihydro-1H-imidazol-2-ylidene)dichloro(3-phenyl-1H-inden-1-ylidene)-(tricyclohexylphosphine)-ruthenium, toluene, 115 °C.

Reagents: (a) $Bu_3P=CHR'$; (b) HF·pyridine. R' = 2-methyl-4-thiazole.

PROCESS FOR THE PREPARATION OF EPOTHILONES

CROSS-REFERENCES TO RELATED APPLICATIONS

This application claims the benefit of U.S. Provisional Application Ser. No. 60/917,572, filed May 11, 2007, and U.S. Provisional Application Ser. No. 60/917,452, filed May 11, 2007, the content of which is incorporated herein by reference.

STATEMENT AS TO RIGHTS TO INVENTIONS MADE UNDER FEDERALLY SPONSORED RESEARCH AND DEVELOPMENT

Work described in this application has been supported, in part, by National Institutes of Health Grant Number 5 R44 CA 093408. The U.S. government has certain rights in the invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The class of polyketides known as epothilones has emerged as a source of potentially therapeutic compounds having modes of action similar to paclitaxel. Interest in the epothilones and epothilone analogs has grown with the observations that certain epothilones are active against tumors that have developed resistance to paclitaxel as well as a reduced potential for undesirable side-effects. Among the epothilones and epothilone analogs being investigated for therapeutic efficacy are the natural product epothilone B, the semi-synthetic epothilone B derivative BMS-247550, also known as ixabepilone, and the synthetic analog EPO-ZK.

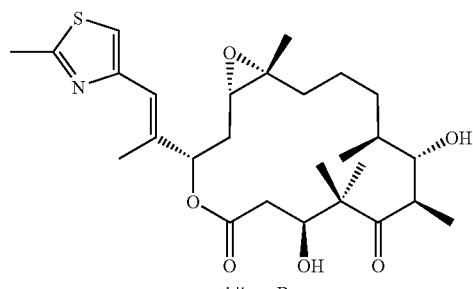

epothilone B

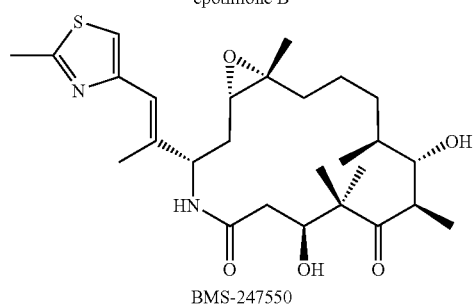

BMS-247550

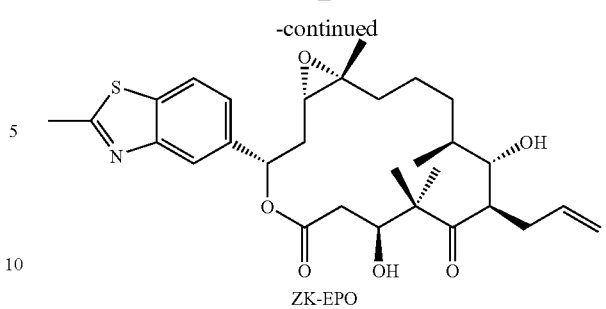

ZK-EPO

Desoxyepothilone B, also known as "epothilone D" is another epothilone derivative having promising anti-tumor properties that is being investigated for therapeutic efficacy. This compound has demonstrated lower toxicity than epothilones having 12, 13-epoxides.

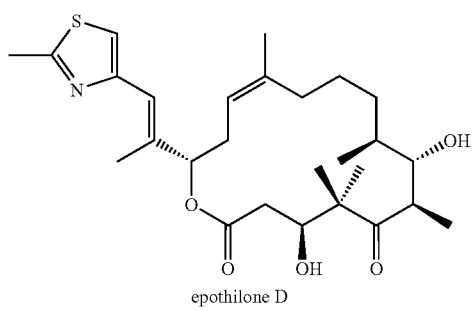

epothilone D

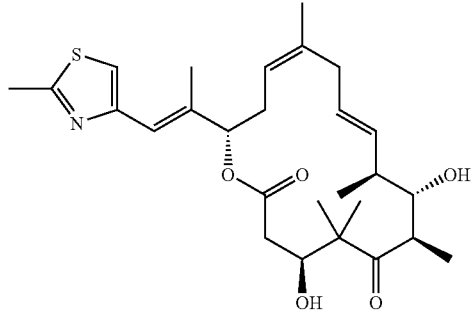

trans-9,10-dehydroepothilone D

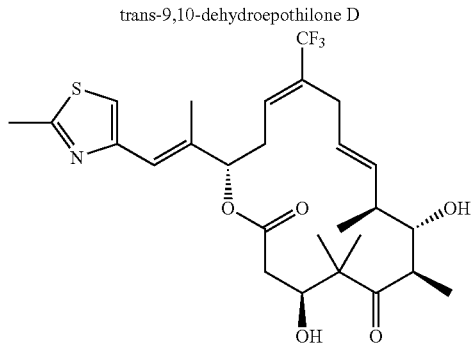

26-trifluoro-trans-9,10-dehydroepothilone D

More recently analogs of epothilone D having greater in vitro potency have been described, including trans-9,10-dehydroepothilone D ((4S,7R,8S,9S,10E,13Z,16S)-4,8-dihydroxy-5,5,7,9,13-pentamethyl-16-[(1E)-1-methyl-2-(2-methyl-4-thiazolyl)ethenyl]-oxacyclohexadeca-10,13-diene-2,6-dione) and its 26-trifluoro-analog, also known as fludelone. These compounds demonstrate remarkable antitumor activity in mouse xenograft models (Rivkin et al., "Discovery of (E)-9,10-dehydroepothilones through Chemical Synthesis: On the Emergence of 26-Trifluoro-(E)-9,10-dehydro-12,13-desoxyepothilone B as a Promising Anticancer Drug Candidate," *J. Am. Chem. Soc.* 126: 10913-10922 (2004).

Although various methods for preparing epothilone derivatives and analogs having anti-tumor activity have been disclosed in the art, including fermentation, semi-synthesis, and total chemical synthesis, there is continuing unmet need for new, more efficient methods for preparing these promising anticancer agents.

BRIEF SUMMARY OF THE INVENTION

The present invention provides new methods and compounds for the preparation of epothilones and epothilone derivatives and analogs, hereafter collectively referred to as "epothilones." According to the invention, methods are provided wherein one or more fragments of the epothilone molecule are obtained through fermentation of organisms and are chemically converted into epothilones. The methods provided by the invention can greatly reduce the cost of manufacture of epothilones, thus facilitating their commercial development as therapeutic agents.

In one aspect, the present invention provides methods for preparing an aldehyde compound having the formula (VI):

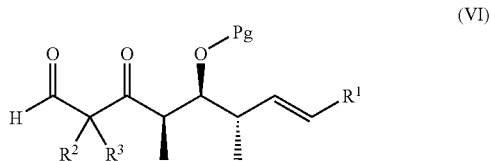

(VI)

wherein Pg and the R groups have the meanings provided below. The methods begin with a compound of formula (IIa) or (IIb), vide infra, and use synthetic transformations to convert (IIa or IIb) into (III); (III) into (IV); (IV) into (V) and ultimately (V) into (VI).

In another aspect, the present invention provides methods for the conversion of (VI) into (VII).

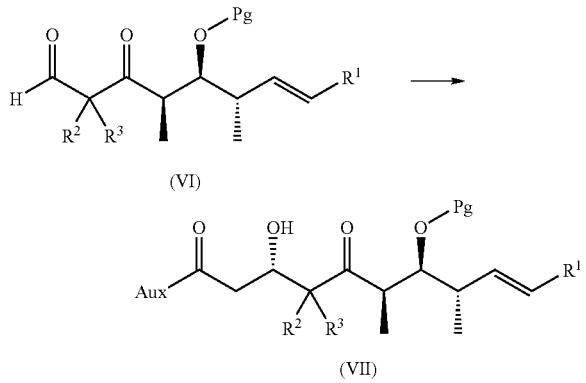

comprising contacting a compound of formula (VI) with a chiral aldol reagent under conditions sufficient to produce said compound of formula (VII), wherein Pg, $R^1$, $R^2$ and $R^3$ have the meaning provided below, and Aux is a chiral auxiliary which produces a diastereomeric ratio of at least 7 to 1 in favor of an S-configuration at the carbon bearing the hydroxy group. The chiral auxiliary serves to direct the stereochemical course of the two-carbon homologation reaction, converting (VI) to (VII).

In yet another aspect, the present invention provides methods for the conversion of (VII) into (IX):

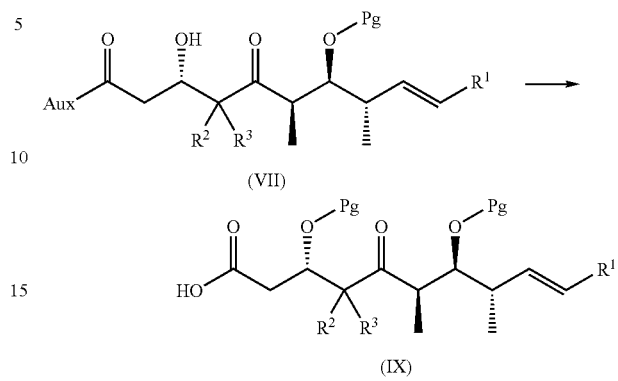

wherein each Pg is an independently selected hydroxy protecting group; $R^1$, $R^2$ and $R^3$ have the meanings provided below; and Aux is a chiral auxiliary; the method comprising:
(a) contacting the compound of formula (VII) with a hydroxy protecting group reagent to attach a protecting group to the hydroxy group; and
(b) hydrolyzing the Aux group to produce the compound of formula (IX). In related aspects, the present invention provides compounds of formula (Ia), (IIb) and (IX'):

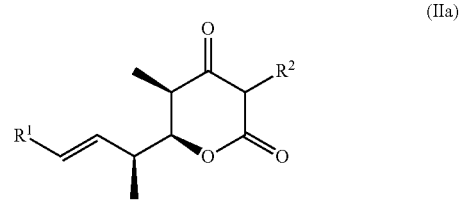

(IIa)

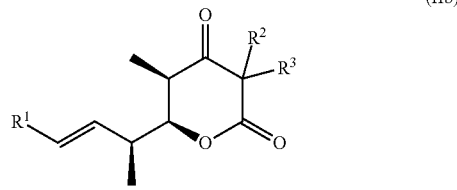

(IIb)

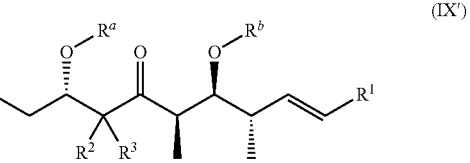

(IX')

wherein the R groups have the meanings provided below.

BRIEF DESCRIPTION OF THE DRAWINGS

FIG. 3 illustrates a series of chemical transformations by which a compound of formula (II) is converted to a compound of formula (III). Specifically, the fermentation product (5R,6S)-3,3,5-trimethyl-6-((S,E)-pent-3-en-2-yl)-dihydro-3H-pyran-2,4-dione (Compound 1) is chemically converted into (3S,6R,7S,8S,E)-3,7-bis(tert-butyldimethyl-silyloxy)-4,4,6,8-tetramethyl-5-oxoundec-9-enoic acid (Compound 9), an intermediate in the chemical synthesis of epothilones.

DETAILED DESCRIPTION OF THE INVENTION

General

Figure 1:
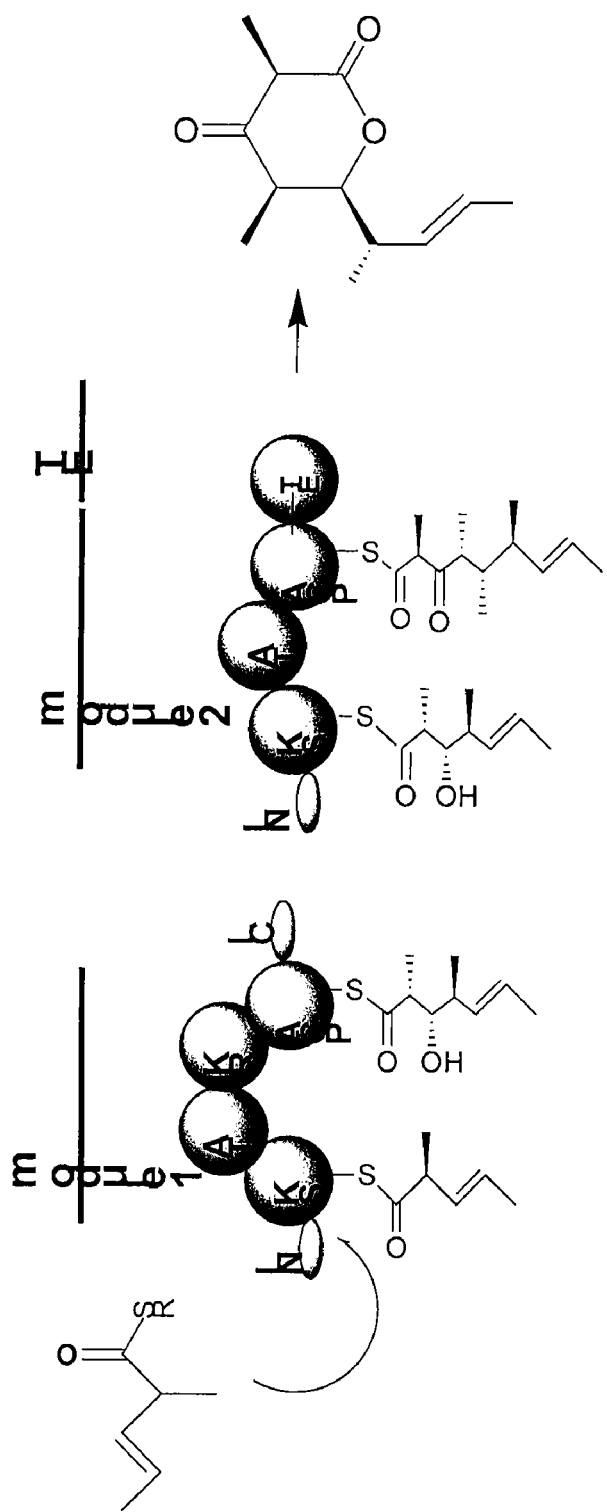
FIG. 1 illustrates the biosynthetic conversion of a compound of formula I to a compound of formula II using a two-module polyketide synthase, to obtain starting materials for the present invention. Specifically, a 2-methyl-3-pentenoate thioester is converted to (5R,6S)-3,3,5-trimethyl-6-((S,E)-pent-3-en-2-yl)-dihydro-3H-pyran-2,4-dione (Compound 1). See also provisional application Ser. No. 60/917,452 and co-pending application Ser. No. 12/118,432.
Figure 2:
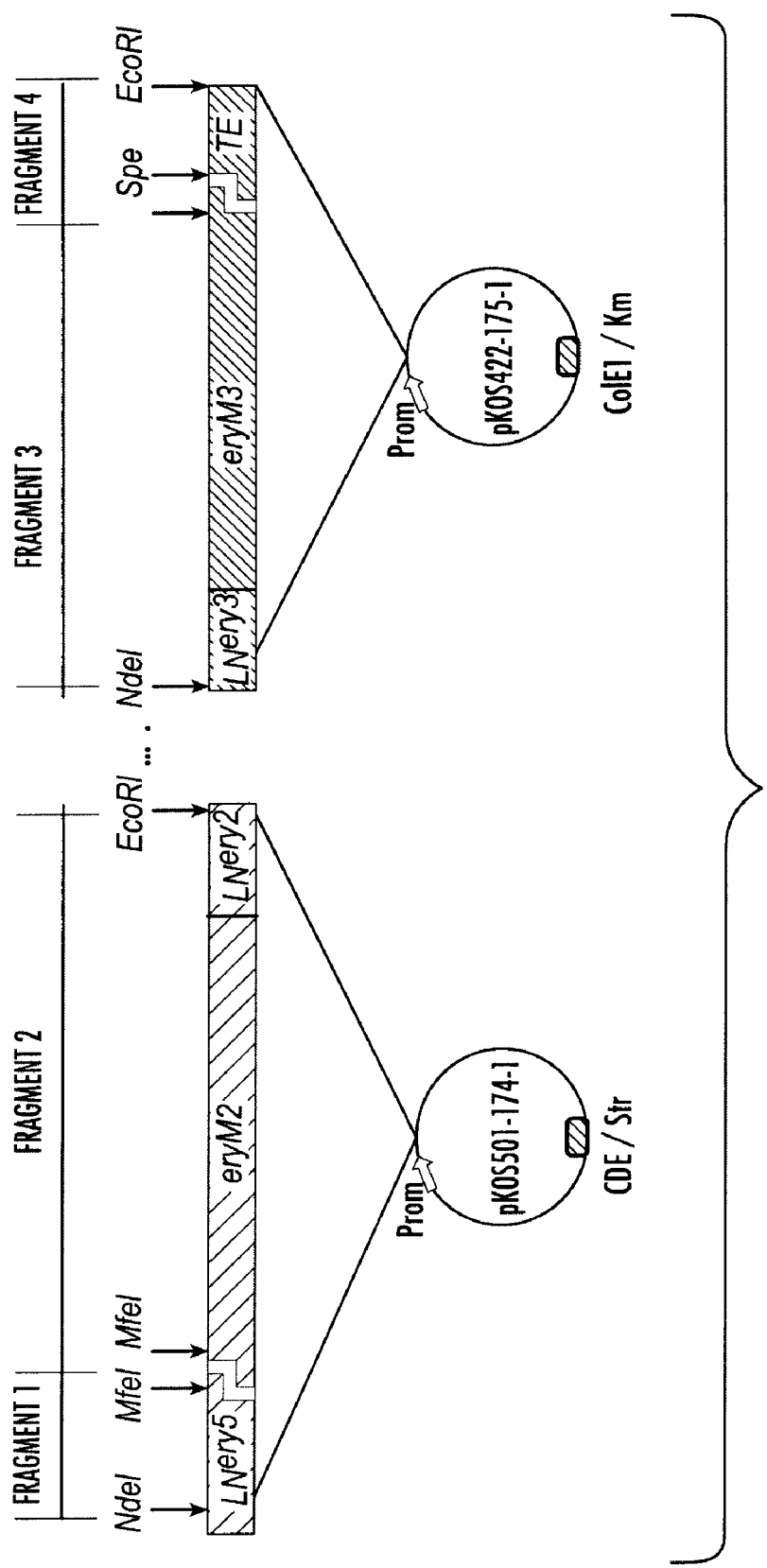
FIG. 2 illustrates two expression plasmids used to express a bimodular polyketide synthase for the production of (5R, 6S)-3,3,5-trimethyl-6-((S,E)-pent-3-en-2-yl)-dihydro-3H-pyran-2,4-dione (Compound 1). Plasmid pKOS501-174-1 contains the ORF for the expression of NL$^{eryM5}$-eryM2-CL$^{eryM2}$ protein inserted between the NdeI and EcoRI site of pCDF-1b (Novagen). Fragment1 comprises the bases 1 to 120 of the DEBS 3 synthetic gene (Genbank accession number AY771999). Fragment2 comprises the bases 6046 to 10636 of the DEBS 1 synthetic gene (Genbank accession number AY771999). Plasmid pKOS422-175-1 contains the ORF for the expression of LN$^{eryYM3}$-eryM3-TE protein inserted between the NdeI and EcoRI site of pET28a (Novagen). Fragment3 comprises the bases 1 to 4412 of the DEBS 2 synthetic gene (GenBank Accession Number AY771999). Fragment4 comprises the bases 8680 to 9504 of the DEBS 3 synthetic gene (Genbank accession number AY771999).

The present invention provides compounds and synthetic methods useful in the preparation of epothilones. By "epothilones" is meant a compound of general structure

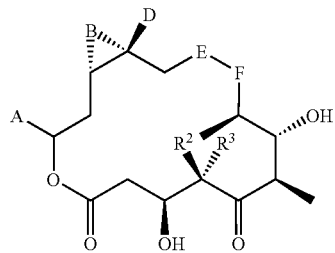

wherein A is aryl, heteroaryl, arylalkenyl, or heteroarylalkenyl; B is —O— or a bond; D is H or unsubstituted or substituted lower alkyl; E-F is C=C or CH$_2$—CH$_2$; and R$^2$ and R$^3$ have the meanings provided below. These compounds include the naturally-occurring epothilones known in the art, for example those described in Hardt et al., "New Natural Epothilones from *Sorangium cellulosum*, Strains So ce90/B2 and So ce90/D13: Isolation, Structure Elucidation, and SAR Studies," *J. Natural Products* 64: 847-56 (2001), as well as synthetic derivatives and analogs thereof, for example epothilone analogs having a 9,10-alkene such as those described in Rivkin et al., "Discovery of (E)-9,10-dehydroepothilones through Chemical Synthesis: On the Emergence of 26-Trifluoro-(E)-9,10-dehydro-12,13-desoxyepothilone B as a Promising Anticancer Drug Candidate," *J. Am. Chem. Soc.* 126: 10913-10922 (2004), each of which is incorporated herein by reference.

In various related aspects the present invention provides novel compounds of formula (I) (structures are provided infra), novel compounds of formula (IIa) and (IIb), and methods for biotransformation of compounds of formula (I) to compounds of formula (IIa) and (IIb). As disclosed herein, compounds of formula (IIa) and (IIb) are valuable chemical intermediates in the synthesis of polyketide precursors of epothilones. Accordingly, the present invention further provides compounds of formulae (III) through (IX) (see General Synthetic Scheme below) and methods for the synthetic conversions described in the General Synthetic Scheme. These and many other aspects of the invention are described in detail below.

Definitions

As used herein, the term "alkyl" refers to a straight or branched, saturated aliphatic radical containing one to ten carbon atoms, unless otherwise indicated e.g., alkyl includes methyl, ethyl, propyl, isopropyl, butyl, sec-butyl, isobutyl, tert-butyl, and the like. The term "lower alkyl" refers to an alkyl radical having from one to four carbon atoms.

The term "aryl" refers to a monocyclic or fused bicyclic ring assembly containing 6 to 10 ring carbon atoms wherein each ring is aromatic e.g., phenyl or naphthyl.

The term "arylalkenyl" refers to a group —R$^x$R$^y$ wherein R$^y$ is an aryl group and R$^x$ is an alkenyl group wherein the alkenyl portions has from one to six carbon atoms and from one to three double bonds. Examples of arylalkenyl groups are styryl, 1-phenylpropen-2-yl, 3-phenyl-propen-1-yl, and the like.

The term "heteroaryl" refers to a monocyclic or fused bicyclic ring assembly containing 6 to 10 ring atoms wherein each ring is aromatic at least one of the ring atoms is a heteroatom (N, O, S). Examples of heteroaryl groups are pyridyl, pyrimidinyl, thienyl, furanyl, thiazolyl, pyrazolyl, oxazolyl, quinolinyl, quinazolinyl, benzofuranyl, benzothiazolyl, benzimidazolyl, and the like.

The term "heteroarylalkenyl" refers to a group —R$^x$R$^y$ wherein R$^y$ is a heteroaryl group and R$^x$ is an alkenyl group wherein the alkenyl portions has from one to six carbon atoms and from one to three double bonds. Examples of heteroarylalkenyl groups are 1-(thiazol-2-yl)ethenyl, 2-(thiazol-2-yl)ethenyl, 2-(2-pyridyl)propen-1-yl, and the like.

The term "substituted" refers to an additional substituent group selected from halogen (preferably fluoro, chloro, or bromo), hydroxy, amino, mercapto, and the like. Preferred substituents for the groups described herein as substituted lower alkyl or substituted alkyl are halogens, particularly fluoro substituents.

As used herein, the term "chiral auxiliary" refers to a group that imparts directional influence to a particular reaction. In the present invention, a chiral auxiliary is used with an aldol condensation to provide a product having a preponderance of one stereochemistry over another stereochemistry. A review of chiral auxiliaries is provided in Evans, ASYMMETRIC SYNTHESIS—THE ESSENTIALS, Christmann and Brase, eds., Wiley-VCH 2007, pages 3-9.

Embodiments of The Invention

The present invention resides in a number of synthetic intermediates and processes for preparing those intermediates as provided in the General Synthetic Scheme below.

wherein $R^5$ is $C_1$-$C_{10}$ alkyl. The conversion of (I) to (IIa) generally is accomplished using fermentation of host cells comprising polyketide synthases. Processes for this transformation are outlined in provisional application Ser. No. 60/917,452, incorporated by reference) and co-pending application Ser. No. 12/118,432, incorporated by referenced). Alternatively, manipulations of the fermentation processes can provide compounds of formula (IIb). In still other

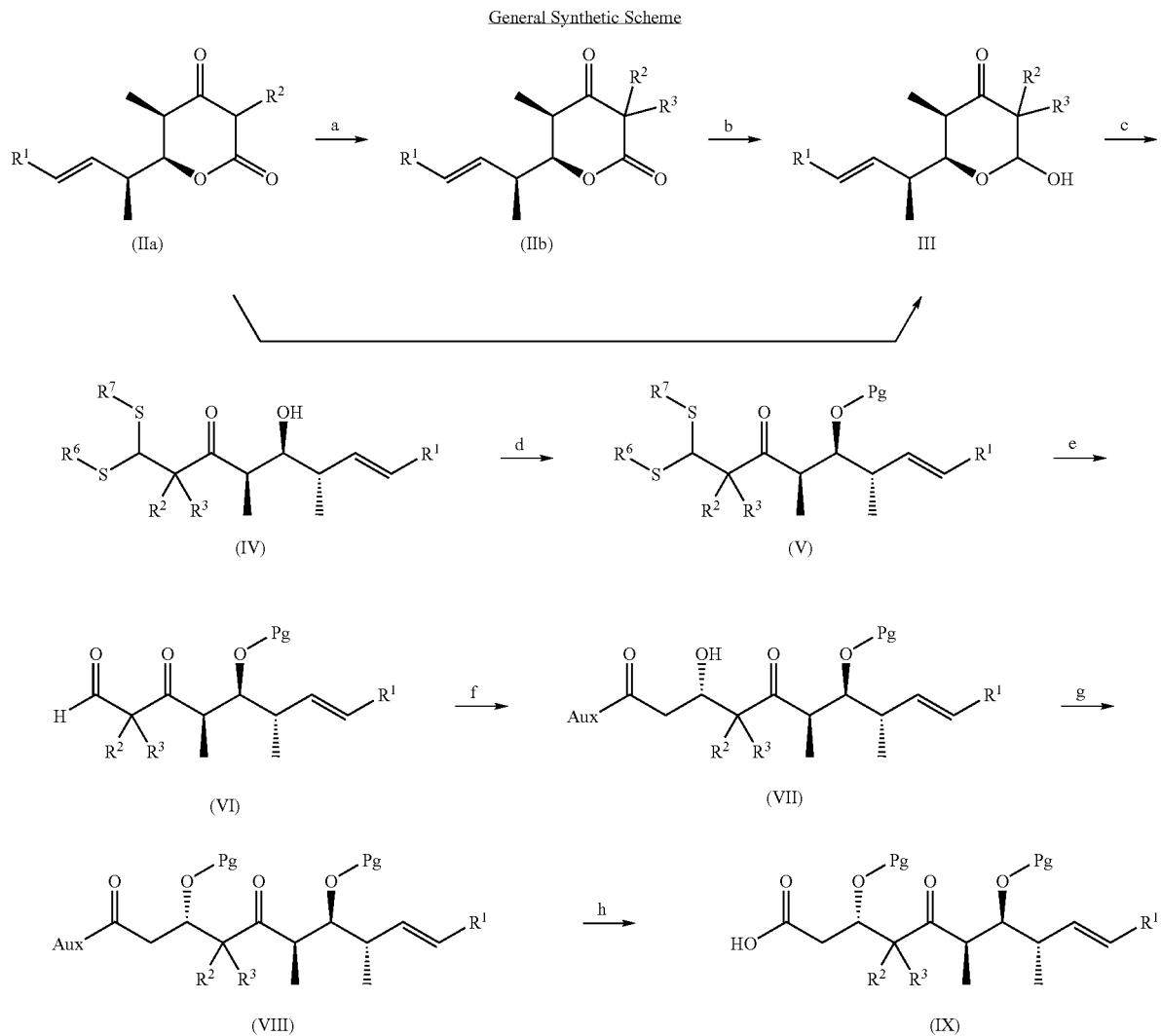

Some starting materials (IIa) in the General Synthetic Scheme (wherein $R^2$ is methyl) can be obtained from (I)

Figure 6:
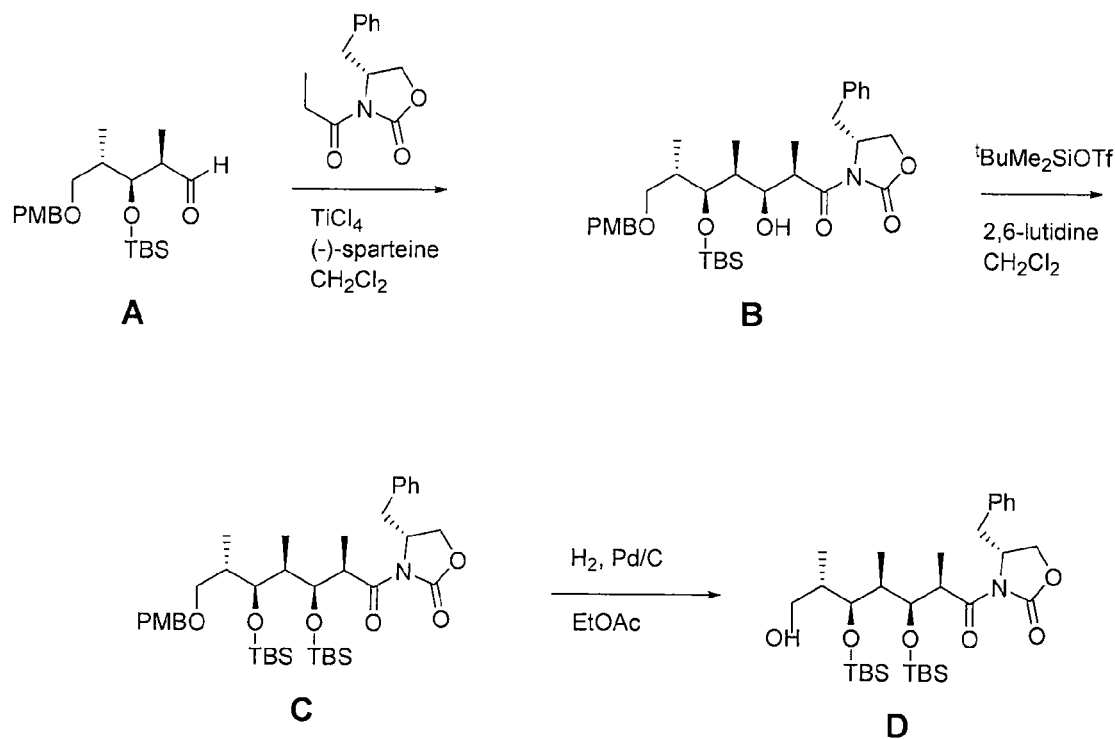
FIGS. 6 and 7 illustrate chemical synthesis schemes for the preparation of a compound of formula (II').
Figure 7:
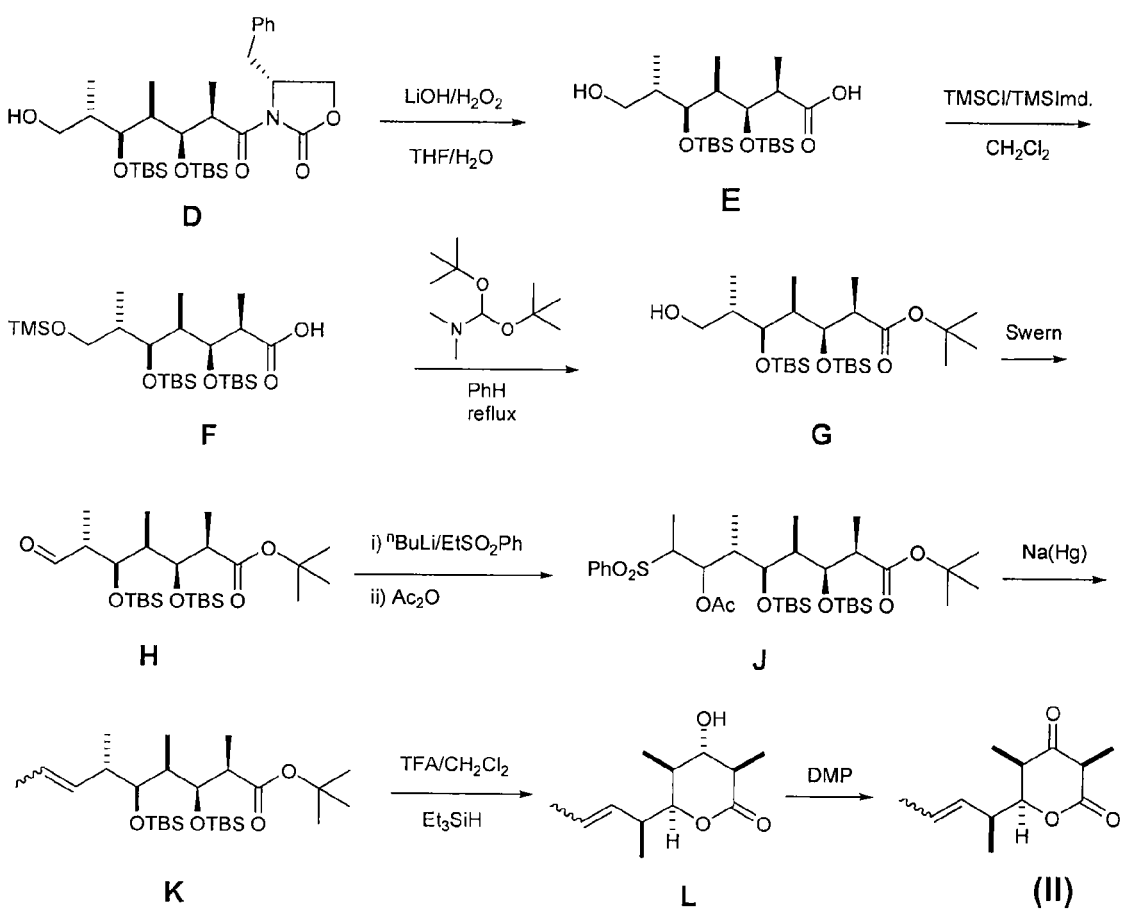

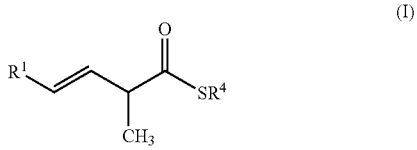

wherein $R^1$ is H, unsubstituted lower alkyl, or substituted lower alkyl; and $R^4$ is $C_1$-$C_{10}$ alkyl, or $CH_2CH_2NH(CO)R^5$, embodiments, the starting compounds of formula (IIa) can be prepared by chemical synthesis as shown in FIGS. 6 and 7 and described in Example 15.

The processes outlined in the Scheme above begin with a keto lactone compound of formula (IIa), in which $R^1$ is H, unsubstituted lower alkyl or substituted lower alkyl and $R^2$ is unsubstituted lower alkyl or substituted lower alkyl. Alkylation of (Ia) provides the geminal disubstituted compounds of formula (IIb), wherein $R^3$ is a substituted or unsubstituted alkyl group. Embodiments of the invention are also provided wherein $R^3$ is hydrogen and (Ia) is converted to (III) directly. Reduction of the lactone carbonyl of either (Ia) or (IIb) provides lactol (III). One of skill in the art will appreciate that while a cyclized embodiment of (III) is shown, the open chain version is also within the scope of the invention. For example:

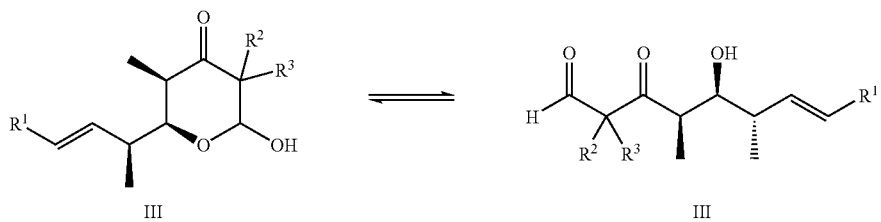

III

Protection of the aldehyde as its dithioacetal produces (IV), wherein each of $R^6$ and $R^7$ is a $C_1$-$C_{10}$ alkyl group, phenyl or benzyl, or $R^6$ and $R^7$ can be combined to form a dithiolane or dithiane ring. Protection of the hydroxy group of (IV) provides (V). The hydroxy protecting group is referred to as Pg and can be any of a variety of protecting groups that are stable to unwanted side reactions and which can be removed under conditions that are not detrimental to the remainder of the molecule. Removal of the dithioacetal provides the aldehyde (VI).

Conversion of (VI) to (VII) involves a two carbon extension using a chiral auxiliary. Protection of the hydroxyl group provides (VIII) which upon removal of the auxiliary yields the carboxylic acid (IX).

Generally, the reactions disclosed herein can be performed under a wide range of conditions, and the solvents and temperature ranges recited below should not be considered limiting. In general, it is desirable for the reactions to be run using mild conditions which will not adversely affect the reactants or the product.

Turning first to step "a" in the General Synthetic Scheme, a compound of formula (II') can be contacted with a variety of alkylating agents, preferably a methylating agent, for example, methyl bromide, methyl iodide or methyl triflate in the presence of a suitable base (e.g., potassium tert-butoxide, sodium hydride or sodium bis(trimethylsilyl)amide) to produce a compound of formula (II). In some embodiments, the compound of formula (II) is isolated. In other embodiments, the compound of formula (II) is carried on directly to step "b". Reaction conditions for step "a" can also be varied. For example, a methylation reaction can proceed at temperatures of from about –78° C. to about 300° C. In one embodiment, the alkylation reaction is a methylation reaction and proceeds at a temperature from about –30° C. to about 150° C. In another embodiment, the methylation reaction is carried out at about room temperature (25° C.), although, in certain other embodiments, the reaction is carried out by heating a compound of formula (II') to an elevated temperature, i.e., about 40° C., 50° C., 60° C., 70° C. or 80° C.

Additionally, the reactions of the inventive methods (including any of steps "a" through "h") are generally carried out in a liquid reaction medium, but in some instances can be run without the addition of a solvent. In one embodiment, the reactions of the invention are conducted in the absence of any solvent. For those reactions conducted in solvent, an inert solvent is preferred, particularly one in which the reaction ingredients are substantially soluble. Typically, the reaction is carried out in the presence of at least one solvent, and possibly, in a combination of two or more solvents. Suitable solvents will depend on the nature of the reactants and will typically include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, xylene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. In certain embodiments, the solvent includes, but is not limited to, acetonitrile, toluene, dimethoxyether, tetrahydrofuran, dioxane, 1,2-dimethoxyethane, bis(2-methoxyethyl)ether, dimethylsulfoxide, dimethylformamide, xylenes, chloroform, dichloromethane, dichloroethane, carbontetrachloride, hexanes, heptane, octane, diethylether and combinations thereof. In other embodiments, the solvent includes acetonitrile or toluene.

Turning next to step "b", the reduction of the lactone to lactol (III) can be accomplished with a number of reducing reagents known to those of skill in the art. In one group of embodiments, the reducing reagent is diisobutylaluminum hydride (DIBAL-H), or similar reagents known to those of skill in the art. Generally, the reduction of (IIa) or (IIb) to (III) is carried out at reduced temperatures (e.g., from –100° C. to about 0° C.). In some embodiments, the reduction is carried out at temperatures of from –100° C. to –30° C., more preferably about –78° C. Suitable solvents are generally aprotic solvents such as chloroform, dichloromethane, dichloroethane, hexanes, heptane, octane, toluene, diethylether and combinations thereof. As with step "a", the lactol product (III) can be isolated or carried on without isolation. When isolated, the product is generally purified via chromatography (e.g., column chromatography or preparative HPLC).

Converting the lactol (III) to a dithioacetal (IV), provided in step "c" of the General Synthetic Scheme, can similarly be accomplished using, for example, HS—$CH_2CH_2$—SH, HS—$CH_2CH_2CH_2$—SH, $C_1$-$C_{10}$ alkyl mercaptan, thiophenol or benzyl mercaptan in the presence of a catalyst (e.g., $BF_3$ etherate, $TiCl_4$ or $Zn(OTf)_2$). As with the previous steps, the dithioacetal product (IV) can be isolated or carried on without isolation. Protection of the hydroxyl group present in the dithioacetal (IV) can be accomplished as noted in step "d" by attachment of a protecting group (Pg). A number of protecting group are suitable and known to those of skill in the art (see, Greene and Wuts, PROTECTIVE GROUPS IN ORGANIC SYNTHESIS, 2nd Ed., Wiley-Interscience, 1991). Preferred hydroxyl protecting groups in the present invention are silyl protecting groups such as trimethylsilyl, tert-butyldimethylsilyl, triethylsilyl, triisopropylsilyl, tert-butyldiphenylsilyl, dimethylhexylsilyl, and the like. Particularly preferred is tert-butyldimethylsilyl. Typically, the silyl ethers (—O-Pg) are formed from the corresponding silyl chlorides, silyl triflates, silyl bromides, and the like (see Greene and Wuts, ibid.).

Removal of the dithio acetal moiety present in compounds of formula (V) to produce the aldehyde (VI) can be accomplished according to standard methods (see Greene and Wuts, ibid.).

In certain embodiments it is preferable to perform the reactions above in solvent and under an inert atmosphere of a gas such as nitrogen or argon.

The reaction processes of the present invention can be conducted in continuous, semi-continuous or batch fashion and may involve a liquid recycle operation as desired. Likewise, the manner or order of addition of the reaction ingredients and solvent are also not generally critical to the success of the reaction, and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. When complete conversion is not desired or not obtainable, the starting materials can be separated from the product and then recycled back into the reaction zone.

The processes may be conducted in either glass lined, stainless steel or similar type reaction equipment (vessel). The reaction zone may be fitted with one or more internal and/or external heat exchanger(s) in order to control undue temperature fluctuations, or to prevent any possible "runaway" reaction temperatures.

Epothilone Intermediates

In view of the General Synthetic Scheme provided above, one aspect of the present invention are the intermediates in the overall epothilone synthesis. Accordingly, compounds of formula IIa, IIb, III, IV, V, VI, VII, VIII and IX all represent specific embodiments of the present invention. Preferred embodiments of the invention are the compounds of formula IIa, IIb, IV, VII and IX.

In one group of embodiments, compounds are provided having the formula:

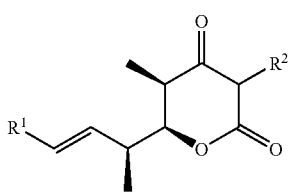

(IIa)

wherein $R^1$ is selected from H, unsubstituted lower alkyl and substituted lower alkyl; and $R^2$ is selected from unsubstituted lower alkyl and substituted lower alkyl. In preferred embodiments, $R^2$ is unsubstituted lower alkyl, more preferably methyl or ethyl. In other preferred embodiments, $R^1$ is selected from H and unsubstituted lower alkyl, more preferably selected from H, methyl and ethyl. Still further preferred are those embodiments in which $R^1$ and $R^2$ are each methyl.

In another group of embodiments, compounds are provided having the formula:

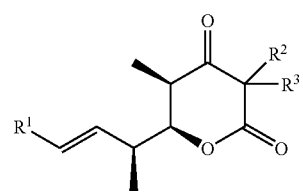

(IIb)

wherein $R^1$ is selected from H, unsubstituted lower alkyl and substituted lower alkyl; $R^2$ is selected from unsubstituted lower alkyl and substituted lower alkyl; and $R^3$ is selected from H, unsubstituted lower alkyl and substituted lower alkyl. In preferred embodiments, $R^2$ is unsubstituted lower alkyl, more preferably methyl or ethyl. In other preferred embodiments, $R^1$ is selected from H and unsubstituted lower alkyl, more preferably selected from H, methyl and ethyl. In still other preferred embodiments, $R^3$ is unsubstituted lower alkyl, more preferably methyl or ethyl. Still further preferred are those embodiments in which $R^1$, $R^2$ and $R^3$ are each methyl.

In still other embodiments, the present invention provides compounds having the formula:

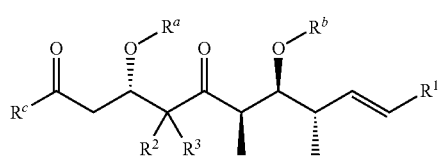

(IX')

wherein $R^a$ and $R^b$ are each independently selected from H and a hydroxy protecting group, wherein the protecting groups can be the same or different for $R^a$ and $R^b$; $R^c$ is selected from OH and a chiral auxiliary (Aux); $R^1$ is selected from H, unsubstituted lower alkyl and substituted lower alkyl; $R^2$ is selected from unsubstituted lower alkyl and substituted lower alkyl; and $R^3$ is selected from H, unsubstituted lower alkyl and substituted lower alkyl; with the proviso that when $R^1$ is H, $R^b$ is t-butyldimethylsilyl and $R^c$ is H, then $R^a$ is other than triethylsilyl. In one group of embodiments, $R^1$ is methyl, $R^a$ and $R^b$ are each t-butyldimethylsilyl and $R^c$ is OH. In another group of embodiments, $R^1$ is methyl, $R^a$ is H, $R^b$ is t-butyldimethylsilyl and $R^c$ is Aux. In yet another group of embodiments, $R^1$ is methyl, $R^a$ and $R^b$ are each t-butyldimethylsilyl and $R^c$ is Aux. For each of the embodiments described with reference to formula (IX'), further preferred are those embodiments in which $R^2$ and $R^3$ are each independently selected from unsubstituted lower alkyl and substituted lower alkyl; more preferably, methyl, ethyl or trifluoromethyl. A variety of chiral auxiliaries useful in the present invention are described in Evans, ASYMMETRIC SYNTHESIS—THE ESSENTIALS, Christmann and Brase, eds., Wiley-VCH 2007, pages 3-9. Preferred auxiliaries include the Oppolzer component, the Helmchen component, the Hoffmann component, the Corey component and the Myers component. More preferably, Aux is the Oppolzer component.

Methods of Preparing Epothilone Intermediates

In another aspect, the present invention is directed to methods of preparing epothilone intermediate as outlined in the General Synthetic Scheme above. The invention is drawn not only to the individual steps illustrated as steps "a" through "h," but also to sequential combinations of those steps, for example steps b+c; c+d; d+e, d+e+f, f+g, f+g+h, and the like.

In one embodiment, the present invention provides methods for preparing aldehyde compounds having the formula (VI)

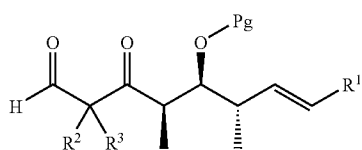

wherein $R^1$ is H, unsubstituted lower alkyl, or substituted lower alkyl; $R^2$ is selected from unsubstituted lower alkyl and substituted lower alkyl; $R^3$ is selected from H, unsubstituted lower alkyl and substituted lower alkyl; and Pg is a hydroxyl protecting group.

In one embodiment of the invention, a compound of formula (VI) is prepared by a sequence of chemical transformations starting with a compound of formula (IIa). Examples 4-8 below demonstrate particular sets of reagents and conditions as illustrations of these transformations.

In a first step, a compound of formula (IIa) is contacted with an alkylating agent, for example $R^3$—X, wherein X is a suitable leaving group in the presence of a base. Preferably, the compound of formula (IIa) is contacted with a methylating agent, for example methyl bromide, methyl iodide, or methyl triflate, and a base, for example potassium tert-butoxide, sodium hydride, or sodium bis(trimethylsilyl)amide, to produce a product of formula (IIb) wherein $R^3$ is methyl, which is optionally isolated.

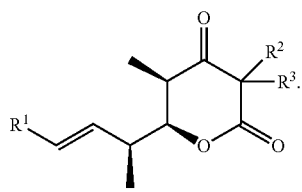

In a second step, the compound of formula (IIb) is contacted with a lactone reducing agent under conditions suitable to form a reduced product of the formula (III), which is optionally isolated.

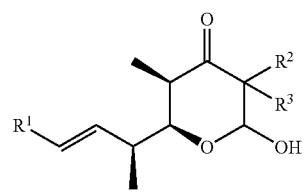

In a third step, the compound of formula (III) is contacted with a dithioacetal-forming reagent (e.g., HS—$(CH_2)_n$—SH, wherein n=2 or 3, a $C_1$-$C_{10}$ alkyl mercaptan, thiophenol or benzyl mercaptan), and a catalyst, for example $BF_3$ etherate, under conditions suitable to form a dithioacetal compound of formula (IV), and optionally isolating the product. Methods of introducing and removing dithioacetal groups are well known in the synthetic art, and are described in Greene and Wuts, PROTECTIVE GROUPS IN ORGANIC SYNTHESIS, $3^{rd}$ edition, which is incorporated herein by reference. In view of the protecting group methods outlined in Greene and Wuts, ibid. one of skill in the art will appreciate that $R^6$ and $R^7$ can each be independently selected from $C_1$-$C_{10}$ alkyl, phenyl and benzyl, or $R^6$ and $R^7$ can optionally be combined to form a dithiolane or dithiane ring. In some preferred embodiments, the dithioacetal-forming reagent (or mercaptan reagent) is selected from 1,2-ethanedithiol, 1,3-propanedithiol, methyl mercaptan, ethyl mercaptan, propyl mercaptan, butyl mercaptan, pentyl mercaptan, benzyl mercaptan and phenyl mercaptan.

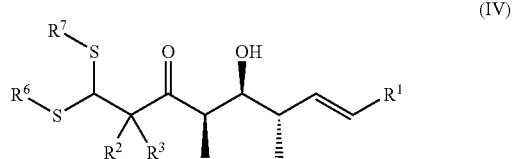

In a fourth step, the compound of formula (IV) is contacted with a hydroxyl protecting group reagent, for example a silyl triflate, under conditions suitable to form a protected compound of the formula (V)

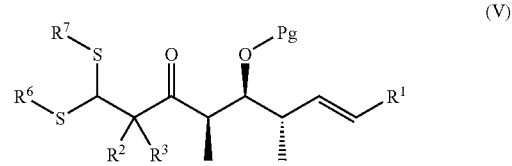

wherein Pg is a hydroxyl protecting group; and optionally isolating the protected compound. Hydroxyl protecting groups and methods of introducing and removing them are also well known in the synthetic art, such as are described in Greene and Wuts, PROTECTIVE GROUPS IN ORGANIC SYNTHESIS, $3^{rd}$ Edition, which is incorporated herein by reference.

In a fifth step, the compound of formula (V) is treated under conditions wherein the dithioacetal is hydrolyzed under conditions suitable to form a product having the formula (VI), and the product is preferably isolated. Reagents and conditions for hydrolysis of dithioacetal groups are well known in the synthetic art, such as are described in Greene and Wuts, ibid.

In the method above, preferred groups for each of $R^1$, $R^2$ and $R^3$ are generally those described above with reference to formulae (IIa), (IIb) and (IX'). In some particularly preferred embodiments, $R^1$ is H or methyl; and $R^2$ and $R^3$ are each selected from substituted lower alkyl and unsubstituted lower alkyl, more preferably, methyl, ethyl or trifluoromethyl. Pg is preferably a silyl group, more preferably t-butyldimethylsilyl, trimethylsilyl or triethylsilyl. In the most preferred embodiments, Pg is a t-butyldimethylsilyl group.

In a first step of the method above, the reducing agent is preferably an aluminum hydride reagent, suitable for lactone to lactol reduction. An example, and preferred, reagent is diisobutylaluminum hydride (DIBAL-H). Following the lactone reduction, the aldehyde form is converted to a dithioacetal, preferably a dithiane or dithiolane using 1,3-propanedithiol or 1,2-ethanedithiol in the presence of a catalyst. Preferred catalysts are Lewis acids, for example, boron trifluoride etherate.

Protection of the hydroxy group following dithioacetal (e.g., dithiane or dithiolane) protection of the aldehyde is accomplished with any of a variety of hydroxy protecting group reagents (see, Greene and Wuts, ibid.). As noted above, in preferred embodiments, the Pg is a silyl group, more preferably t-butyldimethylsilyl, trimethylsilyl or triethylsilyl. In the most preferred embodiments, Pg is a t-butyldimethylsilyl group.

Removal of the dithioacetal (e.g., dithiane or dithiolane) protecting group to form an aldehyde of formula (VI) is carried out by general methods known to those of skill in the art (see, Greene and Wuts, ibid.).

In a related embodiment, the present invention provides methods for the preparation of a compound of formula (VII).

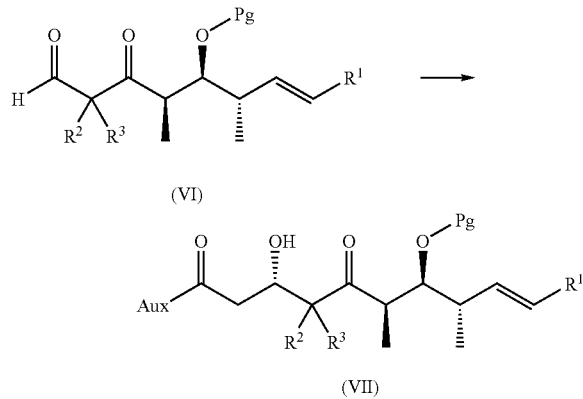

In this method, a compound of formula (VI) is contacted with a chiral aldol reagent under conditions sufficient to produce the compound of formula (VII), wherein Pg is a hydroxy protecting group; $R^1$ is H, unsubstituted lower alkyl or substituted lower alkyl; $R^2$ is selected from unsubstituted lower alkyl and substituted lower alkyl; $R^3$ is selected from H, unsubstituted lower alkyl and substituted lower alkyl; and Aux is a chiral auxiliary which produces a diastereomeric ratio of at least 2 to 1, 3 to 1, 4 to 1, 5 to 1, 6 to 1, or at least 7 to 1 in favor of an S-configuration at the carbon bearing the hydroxy group. In some preferred embodiments, Aux is N-(2R)-bornane-10,2-sultam. In other preferred embodiments, Pg is t-butyldimethylsilyl; $R^1$ is methyl; and Aux is N-(2R)-bornane-10,2-sultam. In each of the embodiments above, preferred are those in which $R^2$ and $R^3$ are each methyl.

In another related embodiment, the present invention provides methods for the preparation of a compound of formula (IX).

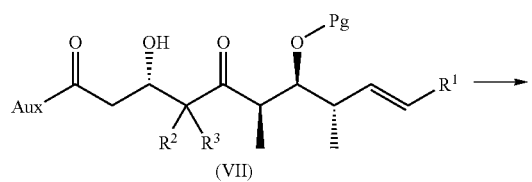

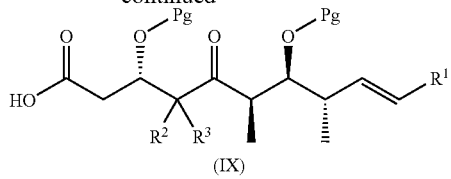

wherein each Pg is an independently selected hydroxy protecting group; $R^1$ is selected from H, unsubstituted lower alkyl and substituted lower alkyl; $R^2$ is selected from unsubstituted lower alkyl and substituted lower alkyl; $R^3$ is selected from H, unsubstituted lower alkyl and substituted lower alkyl; and Aux is a chiral auxiliary. In this method, a compound of formula (VII) is contacted with a hydroxy protecting group reagent to attach a protecting group to the hydroxy group; and the resultant product is hydrolyzed to remove the Aux group to produce the compound of formula (IX). In some preferred embodiments, each Pg is t-butyldimethylsilyl. In other preferred embodiments, each Pg is t-butyldimethylsilyl; $R^1$ is methyl; and Aux is N-(2R)-bornane-10,2-sultam. In each of the embodiments above, particularly preferred are those in which $R^2$ and $R^3$ are each methyl.

Figure 4:
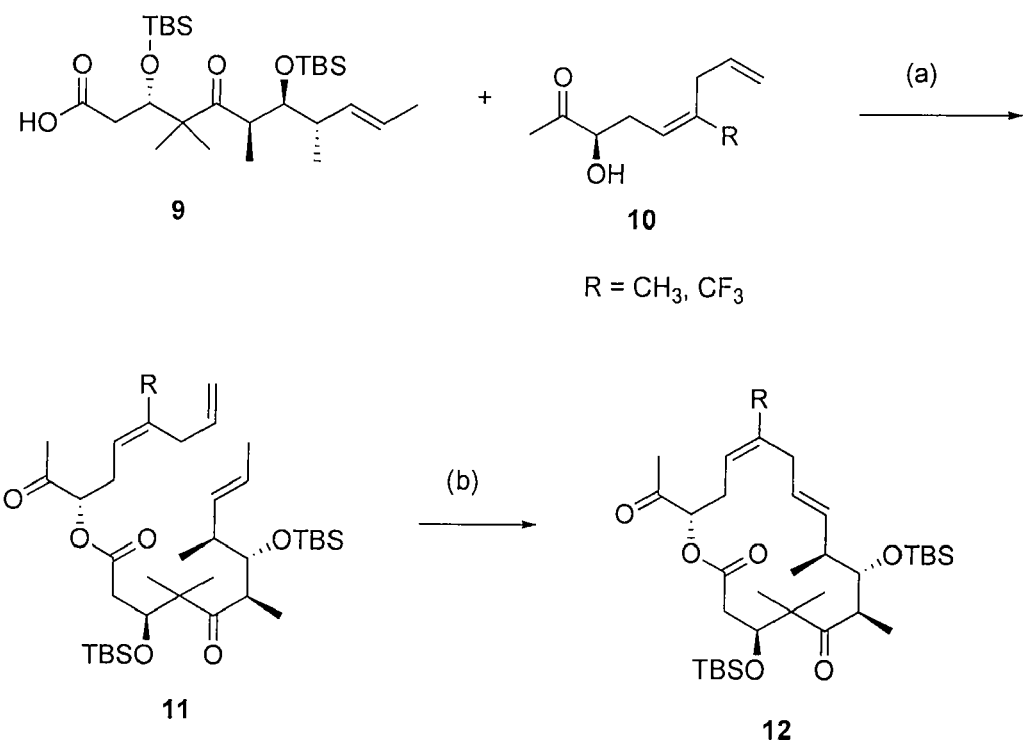
FIG. 4 illustrates one method for the conversion of (3S,6R,7S,8S,E)-3,7-bis(tert-butyldimethylsilyloxy)-4,4,6,8-tetramethyl-5-oxoundec-9-enoic acid (Compound 9) into (4S,7R,8S,9S,10E,13Z,16S)-4,8-dihydroxy-5,5,7,9,13-pentamethyl-16-[1-oxoethyl]oxacyclohexadeca-10,13-diene-2,6-dione (Compound 12), an intermediate in the chemical synthesis of epothilones.

Compounds of formula (IX) are useful in the synthesis of epothilones, as illustrated in Examples 12 and 13 below, and in related FIGS. 4 and 5.

In particular, conversion of (3S,6R,7S,8S,E)-3,7-bis(tert-butyldimethylsilyloxy)-4,4,6,8-tetramethyl-5-oxoundec-9-enoic acid (Compound 9, a compound of formula IX in which each Pg is t-butyldimethylsilyl; $R^1$, $R^2$ and $R^3$ are each methyl) into (4S,7R,8S,9S,10E,13Z,16S)-4,8-dihydroxy-5,5,7,9,13-pentamethyl-16-[1-oxoethyl]oxacyclohexadeca-10,13-diene-2,6-dione (Compound 12), can be accomplished by coupling of Compound 10 (R is $CH_3$ or $CF_3$) to form ester Compound 11, followed by macro-cyclization to form the lactone intermediate, useful in the chemical synthesis of epothilones.

Figure 5:
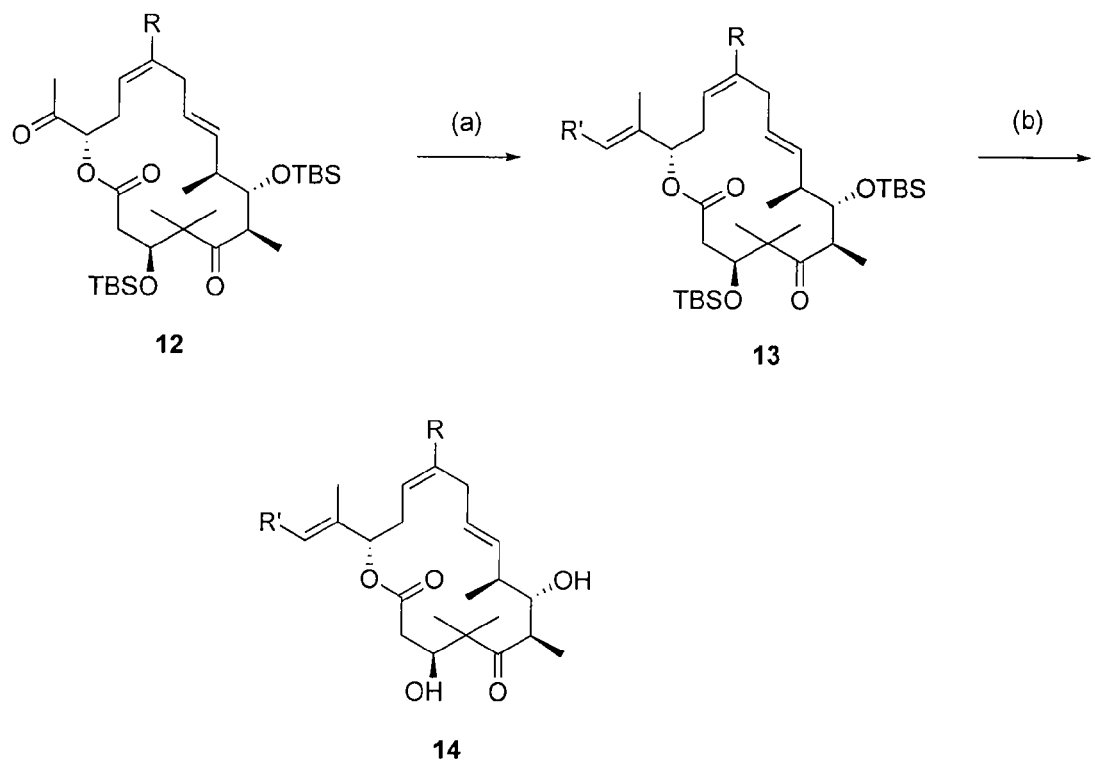
FIG. 5 illustrates one method for the conversion of (4S,7R,8S,9S,10E,13Z,16S)-4,8-dihydroxy-5,5,7,9,13-pentamethyl-16-[1-oxoethyl]-oxacyclohexadeca-10,13-diene-2,6-dione (Compound 12) into trans-9,10-dehydroepothilone D (Compound 14) and 26-trifluoro-trans-9,10-dehydroepothilone D.

As can be seen in FIG. 5, the elaboration of the acetyl moiety present in (4S,7R,8S,9S,10E,13Z,6S)-4,8-dihydroxy-5,5,7,9,13-pentamethyl-16-[1-oxoethyl]-oxacyclo-hexadeca-10,13-diene-2,6-dione (Compound 12) can be accomplished using general Wittig-type reactions to produce protected derivatives (e.g., Compound 13), which upon removal of the protecting groups (illustrated as TBS groups) provides trans-9,10-dehydroepothilone D (Compound 14) and 26-trifluoro-trans-9,10-dehydroepothilone D.

A detailed description of the invention having been provided above, the following examples are given for the purpose of illustrating the present invention and shall not be construed as being a limitation on the scope of the invention or the appended claims. Unless otherwise noted, $^1$H NMR (400 MHz) and $^{13}$C NMR (100 MHz) spectra were recorded in $CDCl_3$ solution at 300 K with a Bruker DRX 400 spectrometer. Chemical shifts were referred to δ 7.26 and 77.0 ppm for $^1$H and $^{13}$C spectra, respectively. High-resolution mass spectrometry (HRMS) was performed by flow injection analysis with manual peak-matching on an Applied Biosystems Mariner TOF spectrometer with a turbo-ion spray source. Infrared spectra were obtained on a Perkin-Elmer Spectrum One FT-IR spectrometer as thin film (neat). Optical rotations were obtained on a Perkin-Elmer-341 digital polarimeter at ambient temperature.

EXAMPLES

Synthesis of Intermediates and Macrolactone

Scheme 1 illustrates a synthetic route to convert 1 to 12.

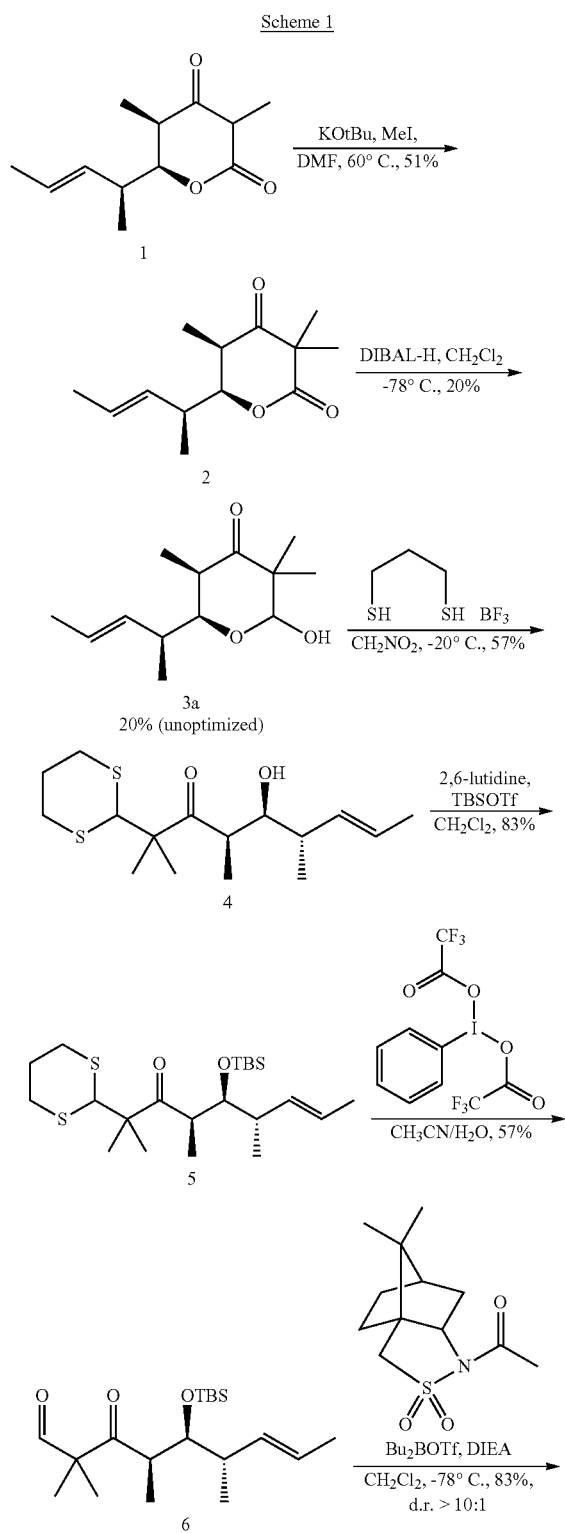

As outlined in Scheme 1, compound 1 was treated with base KOtBu for the deprotonation, and the addition of MeI immediately afforded alkylation product 2, which was reduced to the lactol 3 with DIBAL-H. The polyketide 4 was obtained through Hoffmann's modified trans-thioacetalization using 1,3-propanedithiol/BF$_3$.Et$_2$O. Protection of the hydroxyl group in 4 followed by Danishefsky's oxidation/hydrolysis liberation method[2] successfully provided aldehyde 6. The next aldol condensation applied Oppolzer's sultam, and then compound 7 was obtained from aldehyde 6 in high yield and good diastereoselectivity. The hydroxyl group in 7 was protected with TBS group to obtain compound 8, which was hydrolyzed using LiOH/H$_2$O$_2$ to cleave the sultam auxiliary group and to provide the C1-C9 acid 9. The coupling reaction between acid 9 and alcohol 10 produced ester 11. Finally, the RCM reaction of compound 11 with Nolan's catalyst furnished the 16-member ring product 12, which is completely identical to an authentic sample used in the synthesis of 9,10-dehydro EpoD. Started from the fermentation compound 1, the synthesis of C1-C9 acid 9 was reduced from 18 steps (total chemical synthesis) to 8 steps. A shorter synthetic sequence is provided in Scheme 2, to supply the $C_1$-$C_9$ acid 9 from fermentation product 1 in only 5 steps.

Scheme 2

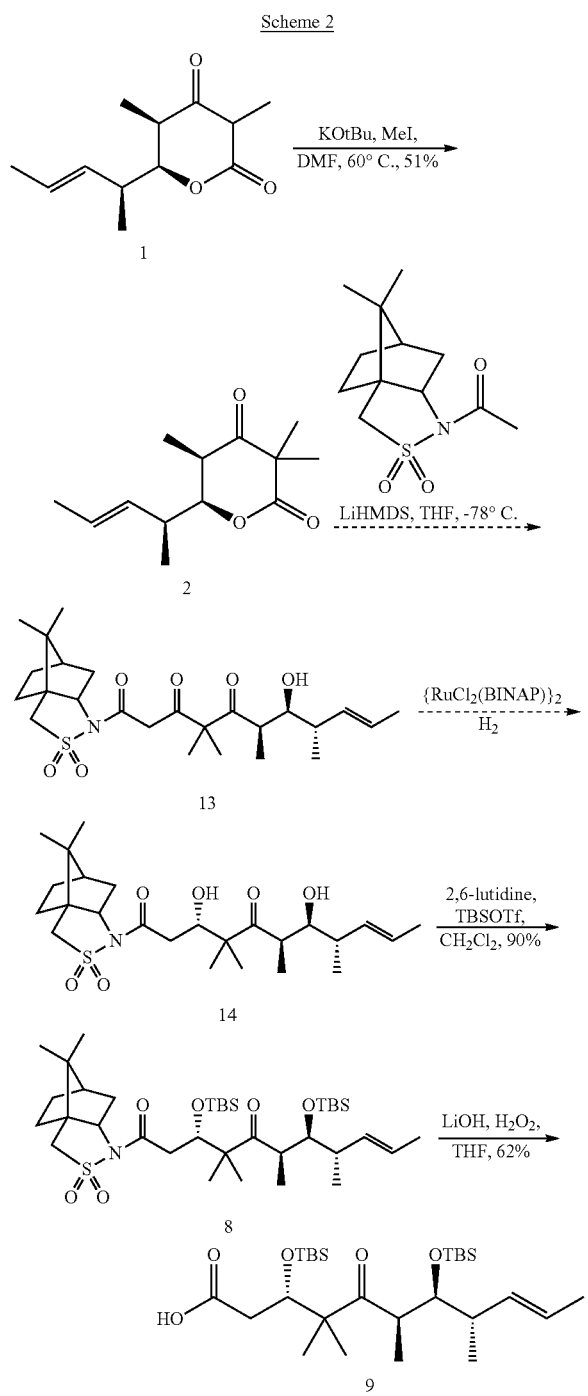

The ring-opening Claisen condensation between 2 and (N-acetyl)-(2R)-bornane-10,2-sultam can provide compound 13, which can be converted to diol 14 through asymmetric hydrogenation. The simple protection of the diol 14 with TBSOTf/lutidine can afford the common precursor 8.

Starting material 1, for each of Scheme 1 and Scheme 2, was obtained according to methods described in application Ser. No. 60/917,452 and co-pending application Ser. No. 12/118,432. Unless otherwise noted, $^1$H NMR (400 MHz) and $^{13}$C NMR (100 MHz) spectra were recorded in CDCl$_3$ solution at 300 K with a Bruker DRX 400 spectrometer. Chemical shifts were referred to δ 7.26 and 77.0 ppm for $^1$H and $^{13}$C spectra, respectively. HRMS were obtained by FIA with manual peak-matching on an Applied Biosystems Mariner TOF spectrometer with a turbo-ion spray source. Infrared spectra were obtained on a Perkin-Elmer Spectrum one FT-IR spectrometer as thin film (neat); Optical rotations were obtained on a Perkin-Elmer-341 digital polarimeter.

Example 1

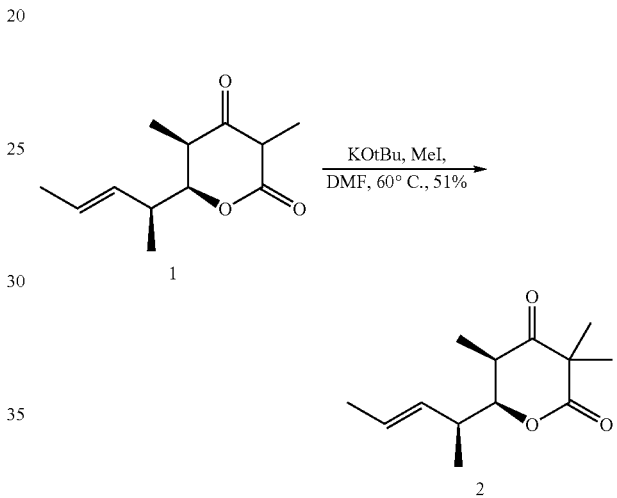

To the solution of 1 (60 mg, 0.29 mmol, 1.0 equiv.) in DMF (3.0 mL) was added KOtBu (0.19 mL, 1.7M in toluene, 0.32 mmol, 1.12 equiv.) at 60° C. The reaction mixture immediately changed from colorless to yellow. Then MeI (0.036 mL, 0.58 mmol, 2.0 equiv.) was added quickly to obtain a colorless solution. The reaction mixture was stirred at 60° C. for 1 minute and the oil bath was removed. The reaction was quenched with phosphate buffer (5 mL, 1.0 M, pH=7), diluted with Et$_2$O (30 mL) and H$_2$O (5 mL). The aqueous layer was extracted with Et$_2$O (10 mL×2) and the combined organic layer was washed with H$_2$O (10 mL×2) and brine (5 mL). And then the organic solution was dried over MgSO$_4$, filtered through a thin pad of silica gel and concentrated. The residue was purified with column chromatography (0% to 10% of EtOAc in hexanes) to obtain compound 2 (33 mg, 51%) as a colorless oil. $R_f$=0.45 (hexane/EtOAc, 4:1); $[α]^{20}_D$ −70.0° (c 1.1, CHCl$_3$); IR (neat) 2978, 2937, 1747, 1715, 1460, 1385, 1280, 1133, 979 cm$^{-1}$; $^1$H NMR (400 MHz, CDCl$_3$) δ 5.57-5.48 (m, 1 H), 5.23 (ddd, J=15.4, 8.0, 1.6 Hz, 1 H), 4.33 (dd, J=5.8, 4.6 Hz, 1 H), 2.95 (ddd, J=14.6, 7.2, 3.4 Hz, 1 H m, 1 H), 2.48 (qd, J=7.0, 7.0, 1H), 1.62 (d, J=6.4 Hz, 3 H), 1.42 (s, 3 H), 1.38 (s, 3 H), 1.13 (d, J=7.2 Hz, 3 H), 1.06 (d, J=6.8 Hz, 3 H). $^{13}$C NMR (100 MHz, CDCl$_3$) δ 209.1, 175.0, 129.5, 129.2, 80.9, 51.6, 42.6, 37.4, 27.0, 21.8, 18.1, 16.9, 9.2; HRMS (ESI TOF) Calcd for $C_{13}H_{21}O_3$ (M$^+$+H), 225.1485. Found 225.1466.

Example 2

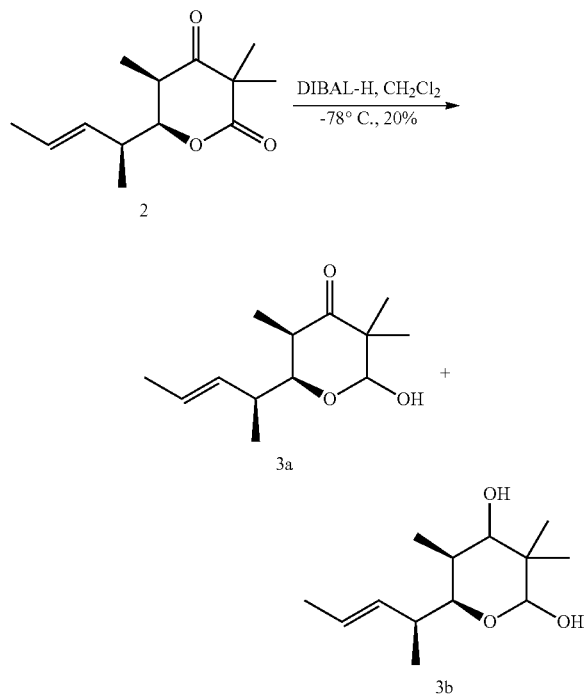

To the solution of 2 (55 mg, 0.244 mmol, 1.0 equiv.) in CH$_2$Cl$_2$ (3 mL) was added DIBAL-H (0.317 mL, 1.0 M in hexanes, 1.3 equiv.) at −78° C. The reaction mixture was stirred at −78° C. for 30 minutes and quenched with sat. citric acid (5 mL), and then diluted with Et$_2$O (20 mL). The aqueous layer was extracted with Et$_2$O (10 mL) and the combined Et$_2$O solution was washed with brine (10 mL), dried over MgSO$_4$, and filtered through a pad of silica gel. The organic solution was concentrated and the residue was purified with column chromatography (0% to 15% of EtOAc in hexanes) to obtain compound 3a (11 mg, 20%) as a pair of diastereomers with 1:1 ratio. R$_f$=0.43 (hexane/EtOAc, 4:1); IR (neat) 3451 (br), 2973, 2934, 2876, 1702, 1453, 1379, 1127, 1099, 1058, 1025, 1007, 971, 939 cm$^{-1}$; $^1$H NMR (400 MHz, CDCl$_3$) δ 5.55-5.36 (m, 2 H), 5.07+4.66 (s, 1 H), 4.13+3.32 (dd, J=9.2, 4.0 Hz, 1 H), 3.46+2.80 (br, 1 H), 2.65-2.57+2.52-2.37 (m, 2 H), 1.71+1.66 (s, 3 H), 1.24-1.07 (m, 9 H), 0.92+0.90 (d, J=7.0 Hz, 3 H). $^{13}$C NMR (100 MHz, CDCl$_3$) δ 215.4+215.0, 134.2+134.0, 125.4+125.2, 100.7+99.4, 77.5+73.4, 50.7+48.9, 45.4+45.2, 37.4+37.1, 25.5, 20.5+20.0, 18.9+18.1, 16.8+16.3, 12.4+12.3; MS Calcd for C$_{13}$H$_{23}$O$_3$ (M$^+$+H), 227. Found 227.

A by-product 3b (27.0 mg, 48%) was obtained. R$_f$=0.13 (hexane/EtOAc, 4:1); IR (neat) 3409(br), 2971, 2916, 1713, 1453, 1378, 1320, 1093, 1041, 1015, 997, 962, 732, 679 cm$^{-1}$; $^1$H NMR (400 MHz, CDCl$_3$) δ 5.52-5.34 (m, 2 H), 4.80+2.76 (s, 1 H), 4.30 (d, J=5.2 Hz, 1 H), 3.87 (d, J=5.6 Hz, 0.5 H), 3.81 (dd, J=10.4, 2.4 Hz, 0.5 H), 3.43 (d, J=5.2 Hz, 1 H), 3.35 (d, J=5.6 Hz, 1 H), 3.06 (dd, J=10.0, 2.4 Hz, 1 H), 2.39-2.28 (m, 1 H), 2.04-1.93 (m, 1 H), 1.66+1.65 (s, 3 H), 1.02-0.085 (m, 12 H); $^{13}$C NMR (100 MHz, CDCl$_3$) δ 135.5+134.7, 124.5+124.4, 101.7+99.7, 79.8+77.2, 73.7+73.4, 41.2+39.3, 37.8+37.3, 36.1+36.0, 24.5+24.2, 20.7, 18.1, 17.0, 16.5, 13.6, 7.1+6.9; HRMS (ESI TOF) Calcd for C$_{13}$H$_{23}$O$_2$ (M$^+$+H—H$_2$O) 211.1693. Found 211.1681.

Recovered starting material (14 mg, 25%) was recycled.

Example 3

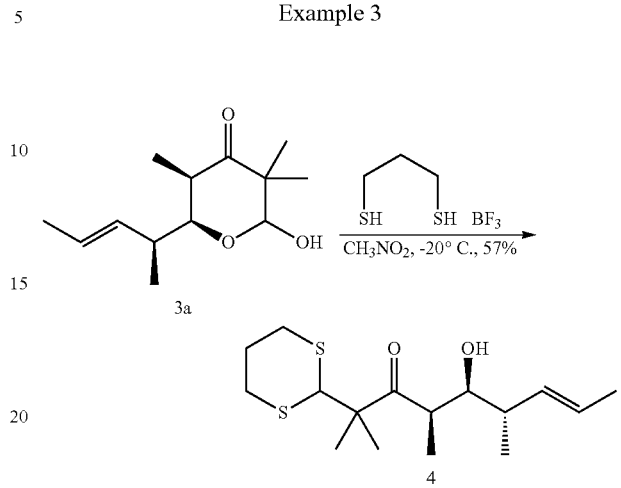

To the solution of 3a (90 mg, 0.4 mmol, 1.0 equiv.) in nitromethane (1 mL) was added propane-1,3-dithiol (0.08 mL, 0.8 mmol, 2.0 equiv.) and BF$_3$.OEt$_2$ (0.151 mL, 1.2 mmol, 3.0 equiv.) at −20° C. The reaction mixture was stirred at −20° C. for 12 hours, and then was quenched with sat. NaHCO$_3$ (20 mL) and diluted with Et$_2$O (30 mL). The aqueous layer was extracted with Et$_2$O (10 mL) and the combined organic layer was dried over MgSO$_4$, filtered and concentrated. The residue was purified with column chromatography (0% to 12% of EtOAc in hexanes) to obtain product 4 (66.8 mg, 52%) as a colorless oil. R$_f$=0.47 (hexane/EtOAc, 4:1); [α]$^{20}_D$ −39.2° (c 1.0, EtOH); IR (neat) 3508 (br), 2970, 2935, 2901, 1690, 1460, 1422, 1368, 1277, 976, 908, 731 cm$^{-1}$; $^1$H NMR (400 MHz, CDCl$_3$) δ 5.53-5.40 (m, 2 H), 4.42 (s, 1 H), 3.57 (dd, J=8.0, 2.0 Hz, 1 H), 3.16 (qd, J=6.8, 2.0 Hz, 1 H), 3.07 (m, 1 H), 2.94-2.80 (m, 4 H), 2.25-2.05 (m, 2 H), 1.86-1.73 (m, 1 H), 1.66 (d, J=7.2 Hz, 3 H), 1.31 (s, 3 H), 1.29 (s, 3 H), 1.09 (d, J=6.8 Hz, 3 H), 0.96 (d, J=7.6 Hz, 3 H); $^{13}$C NMR (100 MHz, CDCl$_3$) δ 218.6, 133.7, 125.5, 74.6, 57.0, 53.0, 41.3, 39.6, 31.3, 25.9, 22.5, 22.2, 18.3, 18.0, 17.3, 10.8. HRMS (ESI TOF) Calcd for C$_{16}$H$_{28}$O$_2$NaS$_2$ (M$^+$+Na), 339.1423. Found 339.1441.

Example 4

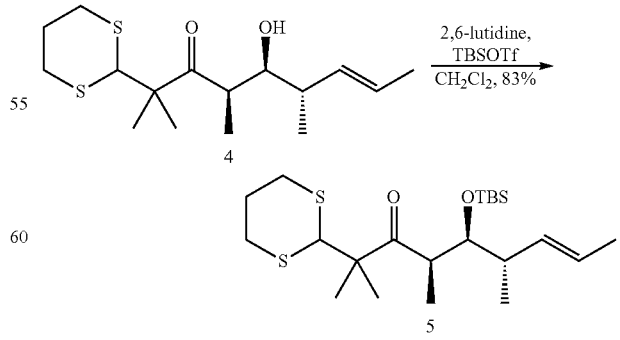

To the solution of 4 (60 mg, 0.19 mmol, 1.0 equiv.) in CH$_2$Cl$_2$ (1 mL) was added 2,6-lutidine (0.13 mL, 1.14 mmol, 6.0 equiv.) and TBSOTf (0.13 mL, 0.57 mmol, 3.0 equiv.) at −45° C. The reaction mixture was warmed up to −20° C. slowly in 10 minutes, and stirred at the same temperature for 1 hr. Then the reaction mixture was quenched with sat. NaHCO$_3$ (15 mL) and diluted with Et$_2$O (20 mL). The aqueous layer was extracted with Et$_2$O (10 mL×2) and the combined organic layer was dried over Na$_2$SO$_4$, filtered and concentrated. The residue was purified with column chromatography (0% to 4% of EtOAc in hexanes) to obtain product 5 (68 mg, 83%) as a colorless oil. R$_f$=0.69 (hexane/EtOAc, 9:1); [α]$^{20}_D$−38.8° (c 1.0, EtOH); IR (neat) 2957, 2931, 2896, 2856, 1700, 1462, 1368, 1252, 1115, 1068, 1028, 986, 875, 833, 773 cm$^{-1}$; $^1$H NMR (400 MHz, CDCl$_3$) δ 5.43-5.39 (m, 2 H), 3.83 (dd, J=6.0, 2.8 Hz, 1 H), 3.02 (p, J=7.2, Hz, 1 H), 2.89-2.76 (m, 4 H), 2.11-2.01 (m, 2 H), 1.80-1.75 (m, 1 H), 1.62 (d, J=5.2 Hz, 3 H), 1.27 (s, 3 H), 1.21 (s, 3 H), 1.03 (d, J=7.2 Hz, 3 H), 0.95 (d, J=6.8 Hz, 3 H), 0.87 (s, 9 H), 0.03 (s, 3 H), 0.01 (s, 3 H); $^{13}$C NMR (100 MHz, CDCl$_3$) δ 215.7, 132.7, 125.5, 75.8, 57.0, 52.5, 44.6, 42.7, 31.2, 26.1, 26.0, 23.2, 22.1, 18.5, 18.4, 18.2, 15.2, −3.7, −4.1.

Example 5

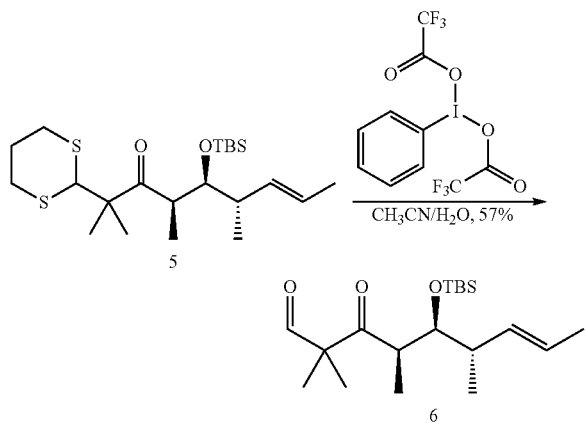

To the solution of 5 (64 mg, 0.149 mmol, 1.0 equiv.) in CH$_3$CN/H$_2$O (6:1, 3.5 mL) was added [bis(trifluoroacetoxy)]iodobenzene (96 mg, 0.223 mmol, 1.5 equiv.) at room temperature. The reaction mixture was stirred at room temperature for 20 minutes, quenched with NaHCO$_3$ (6 mL), and diluted with Et$_2$O (30 mL). The aqueous layer was extracted with Et$_2$O (5 mL×2). The combined organic layer was washed with H$_2$O (5 mL), brine (10 mL), filtered and concentrated. The residue was purified with column chromatography (0% to 4% of EtOAc in hexanes) to obtain aldehyde 6 (28.7 mg, 57%) as a colorless oil. R$_f$=0.38 (hexane/EtOAc, 9:1); [α]$^{20}_D$−22.5° (c 1.0, EtOH); IR (neat) 2958, 2932, 1747, 2885, 2858, 1736, 1699, 1691, 1463, 1362, 1253, 1082, 1029, 974, 875, 835, 774, 674 cm$^{-1}$; $^1$H NMR (400 MHz, CDCl$_3$) δ 9.50 (s, 1 H), 5.29-5.23 (m, 2 H), 3.82 (dd, J=7.6, 2.8 Hz, 1 H), 2.90 (p, J=7.2, Hz, 1 H), 2.07-2.02 (m, 1 H), 1.57 (d, J=5.0 Hz, 3 H), 1.25 (s, 3 H), 1.24 (s, 3 H), 0.95 (d, J=7.2 Hz, 3 H), 0.91 (d, J=7.2 Hz, 3 H), 0.84 (s, 9 H), 0.02 (s, 3 H), −0.01 (s, 3 H); $^{13}$C NMR (100 MHz, CDCl$_3$) δ 212.6, 200.4, 132.5, 125.6, 75.8, 60.7, 46.2, 42.2, 26.0, 20.0, 19.8, 18.2, 18.0, 17.3, 15.2, −3.9, −4.1; MS Calcd for C$_{19}$H$_{36}$O$_3$Si (M$^+$+H), 341. Found 341.

Example 6

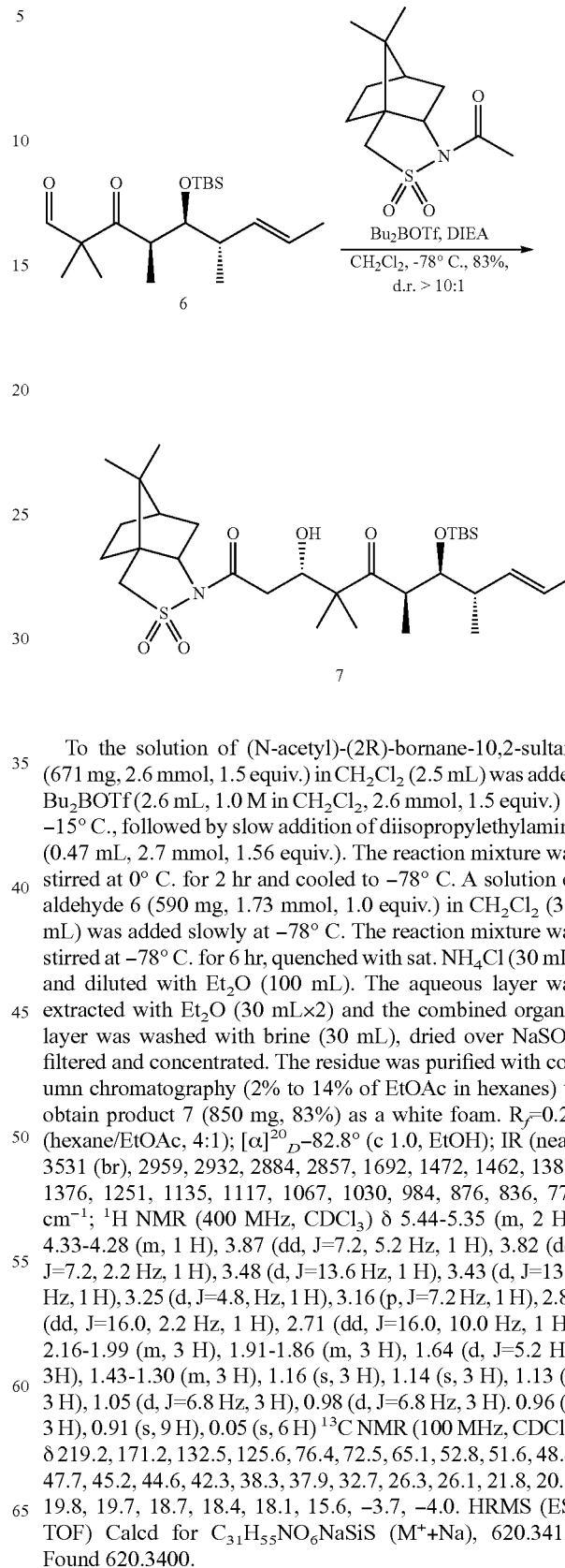

To the solution of (N-acetyl)-(2R)-bornane-10,2-sultam (671 mg, 2.6 mmol, 1.5 equiv.) in CH$_2$Cl$_2$ (2.5 mL) was added Bu$_2$BOTf (2.6 mL, 1.0 M in CH$_2$Cl$_2$, 2.6 mmol, 1.5 equiv.) at −15° C., followed by slow addition of diisopropylethylamine (0.47 mL, 2.7 mmol, 1.56 equiv.). The reaction mixture was stirred at 0° C. for 2 hr and cooled to −78° C. A solution of aldehyde 6 (590 mg, 1.73 mmol, 1.0 equiv.) in CH$_2$Cl$_2$ (3.0 mL) was added slowly at −78° C. The reaction mixture was stirred at −78° C. for 6 hr, quenched with sat. NH$_4$Cl (30 mL) and diluted with Et$_2$O (100 mL). The aqueous layer was extracted with Et$_2$O (30 mL×2) and the combined organic layer was washed with brine (30 mL), dried over NaSO$_4$, filtered and concentrated. The residue was purified with column chromatography (2% to 14% of EtOAc in hexanes) to obtain product 7 (850 mg, 83%) as a white foam. R$_f$=0.27 (hexane/EtOAc, 4:1); [α]$^{20}_D$−82.8° (c 1.0, EtOH); IR (neat) 3531 (br), 2959, 2932, 2884, 2857, 1692, 1472, 1462, 1389, 1376, 1251, 1135, 1117, 1067, 1030, 984, 876, 836, 774 cm$^{-1}$; $^1$H NMR (400 MHz, CDCl$_3$) δ 5.44-5.35 (m, 2 H), 4.33-4.28 (m, 1 H), 3.87 (dd, J=7.2, 5.2 Hz, 1 H), 3.82 (dd, J=7.2, 2.2 Hz, 1 H), 3.48 (d, J=13.6 Hz, 1 H), 3.43 (d, J=13.6 Hz, 1 H), 3.25 (d, J=4.8, Hz, 1 H), 3.16 (p, J=7.2 Hz, 1 H), 2.85 (dd, J=16.0, 2.2 Hz, 1 H), 2.71 (dd, J=16.0, 10.0 Hz, 1 H), 2.16-1.99 (m, 3 H), 1.91-1.86 (m, 3 H), 1.64 (d, J=5.2 Hz, 3H), 1.43-1.30 (m, 3 H), 1.16 (s, 3 H), 1.14 (s, 3 H), 1.13 (s, 3 H), 1.05 (d, J=6.8 Hz, 3 H), 0.98 (d, J=6.8 Hz, 3 H). 0.96 (s, 3 H), 0.91 (s, 9 H), 0.05 (s, 6 H) $^{13}$C NMR (100 MHz, CDCl$_3$) δ 219.2, 171.2, 132.5, 125.6, 76.4, 72.5, 65.1, 52.8, 51.6, 48.4, 47.7, 45.2, 44.6, 42.3, 38.3, 37.9, 32.7, 26.3, 26.1, 21.8, 20.8, 19.8, 19.7, 18.7, 18.4, 18.1, 15.6, −3.7, −4.0. HRMS (ESI TOF) Calcd for C$_{31}$H$_{55}$NO$_6$NaSiS (M$^+$+Na), 620.3412. Found 620.3400.

Example 7

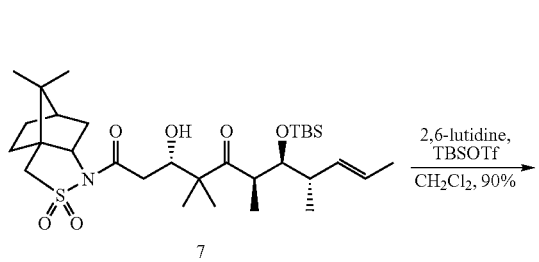

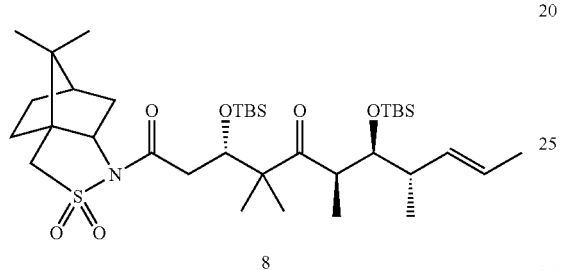

To the solution of compound 7 (614 mg, 1.026 mmol, 1.0 equiv.) in CH$_2$Cl$_2$ (6.0 mL) was added 2,6-lutidine (0.36 mL, 3.08 mmol, 3.0 equiv.) and TBSOTf (0.472 mL, 2.052 mmol, 2.0 equiv.) at −45° C. The reaction mixture was warmed up slowly to −30° C. in 1 hr, quenched with water (10 mL), and diluted with Et$_2$O (30 mL). The aqueous layer was extracted with Et$_2$O (10 mL×2) and the combined organic layer was dried over MgSO$_4$, filtered and concentrated. The residue was purified with column chromatography (0% to 15% of EtOAc in hexanes) to obtain product 8 (658 mg, 90%) as a white foam. R$_f$=0.58 (hexane/EtOAc, 4:1); $[\alpha]^{20}{}_D$-65.9° (c 1.0, EtOH); IR (neat) 3531 (br), 2957, 2930, 2885, 2857, 1693, 1472, 1462, 1388, 1332, 1311, 1251, 1135, 1084, 1030, 984, 876, 834, 774, 733 cm$^{-1}$; $^1$H NMR (400 MHz, CDCl$_3$) δ 5.52-5.46 (m, 1 H), 5.39-5.34 (m, 1 H), 4.55 (t, J=4.4 Hz, 1 H), 3.86 (dd, J=8.0, 4.8 Hz, 1 H), 3.76 (dd, J=8.0, 2.0 Hz, 1 H), 3.45 (d, J=13.6 Hz, 1 H), 3.39 (d, J=13.6 Hz, 1 H), 3.16 (p, J=7.2 Hz, 1 H), 2.90 (dd, J=17.6, 4.4 Hz, 1 H), 2.60 (dd, J=17.6, 4.0 Hz, 1 H), 2.27-2.22 (m, 1 H), 2.11-1.99 (m, 2 H), 1.90-1.85 (m, 3 H), 1.65 (dd, J=6.2, 0.6 Hz, 3 H), 1.39-1.32 (m, 2 H), 1.18 (s, 3 H), 1.15 (s, 3 H), 1.08 (s, 3 H), 1.01 (d, J=7.2 Hz, 3 H), 0.96 (d, J=7.2 Hz, 3 H). 0.95 (s, 3H), 0.90 (s, 9 H), 0.86 (s, 9 H), 0.10 (s, 3 H), 0.05 (s, 3 H), 0.04 (s, 3 H), 0.03 (s, 3 H); $^{13}$C NMR (100 MHz, CDCl$_3$) δ 218.2, 170.1, 132.2, 125.7, 76.8, 72.0, 65.1, 54.1, 53.0, 48.3, 47.7, 45.9, 44.7, 42.0, 41.9, 38.3, 32.8, 26.4, 26.2, 25.9, 23.5, 20.8, 19.9, 19.7, 18.5, 18.2, 18.0, 15.6, −3.5, −3.9, −4.3, −5.1; HRMS (ESI TOF) Calcd for C$_{37}$H$_{69}$NO$_6$NaSi$_2$S (M$^+$+Na), 734.4276. Found 734.4251.

Example 8

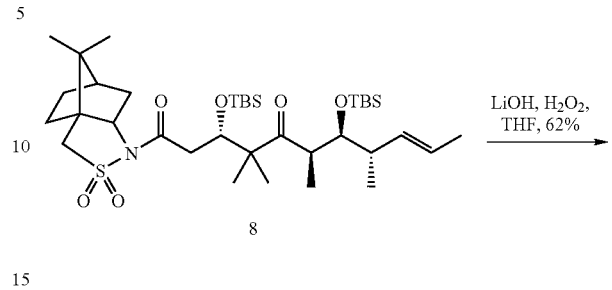

To the solution of compound 8 (170 mg, 0.239 mmol, 1.0 equiv.) in THF (10.4 mL) and H$_2$O (2.6 mL) was added LiOH.H$_2$O (150 mg, 3.60 mmol, 15.0 equiv.) and H$_2$O$_2$ (3.2 mL, 38.9 mmol, 162 equiv.), at 0° C. The reaction mixture was stirred at room temperature for 12 hours, quenched slowly with NaHSO$_3$ (1.0 M, 50 mL) at 0° C.; and then was concentrated to about 8 mL and diluted Et$_2$O (20 mL). The aqueous layer was extracted with Et$_2$O (10 mL×2) and the combined organic layer was dried over MgSO$_4$, filtered and concentrated. The residue was purified with column chromatography (1% to 25% of EtOAc in hexanes, 5% of HOAc was added to the EtOAc) to obtain acid 9 (76 mg, 62%) as a colorless oil. R$_f$=0.58 (hexane/EtOAc, 4:1); $[\alpha]^{20}{}_D$-23.1° (c 1.0, CH$_3$Cl); IR (neat) 3531 (br), 2957, 2930, 2886, 2857, 1712, 1696, 1473, 1253, 1087, 1030, 987, 834, 775 cm$^{-1}$; $^1$H NMR (400 MHz, CDCl$_3$) δ 5.49-5.37 (m, 2 H), 4.37 (dd, J=6.8, 2.8 Hz, 1 H), 3.81 (dd, J=7.2, 2.2 Hz, 1 H), 3.05 (p, J=6.8 Hz, 1 H), 2.50 (dd, J=16.4, 2.8 Hz, 1 H), 2.30 (dd, J=16.4, 7.2 Hz, 1 H), 2.09-2.04 (m, 1 H), 1.66 (d, J=5.6 Hz, 3 H), 1.20 (s, 3 H), 1.09 (s, 3 H), 1.02 (d, J=7.2 Hz, 3 H), 0.99 (d, J=7.2 Hz, 3 H). 0.92 (s, 9 H), 0.88 (s, 9 H), 0.09 (s, 3 H), 0.06 (br, 6 H), 0.04 (s, 3 H); $^{13}$C NMR (100 MHz, CDCl$_3$) δ 218.6, 178.5, 132.7, 126.0, 76.7, 73.8, 53.7, 46.2, 42.6, 40.4, 26.5, 26.2, 24.2, 19.4, 19.2, 18.7, 18.5, 18.4, 15.1, −3.6, −4.0, −4.4, −4.7; HRMS (ESI TOF) Calcd for C$_{27}$H$_{54}$O$_5$NaSi$_2$ (M$^+$+Na), 537.3402. Found 537.3405.

Example 9

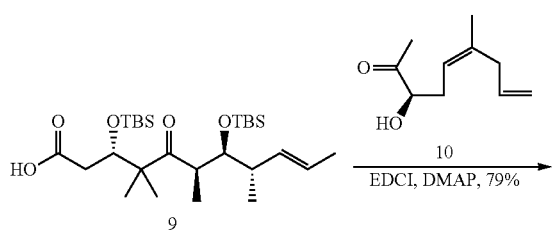

-continued

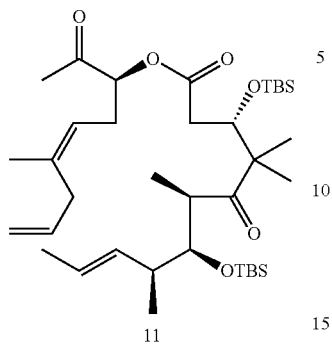

11

To the solution of acid 9 (74 mg, 0.14 mmol, 1.0 equiv.) and alcohol 10 (84 mg, 0.5 mmol, 3.5 equiv.) in CH$_2$Cl$_2$ (0.8 mL) was added DMAP (34 mg, 0.28, 2.0 equiv.) and EDCI (107 mg, 0.56 mmol, 4.0 equiv.). The reaction mixture was stirred at room temperature for 2 hours, and diluted with Et$_2$O (50 mL). The aqueous layer was extracted with Et$_2$O (10 mL×2) and the combined organic layer was dried over MgSO$_4$, filtered and concentrated. The residue was purified with column chromatography (0% to 10% of EtOAc in hexanes) to obtain acid 11 (72 mg, 79%) as a colorless oil. R$_f$=0.71 (hexane/EtOAc, 4:1); [α]$^{20}_D$-28.0° (c 1.0, CHCl$_3$); IR (neat) 2956, 2930, 2857, 1743, 1732, 1695, 1638, 1473, 1379, 1361, 1252, 1162, 1071, 988, 831, 775 cm$^{-1}$; $^1$H NMR (400 MHz, CDCl$_3$) δ 5.75-5.66 (m, 1 H), 5.51-5.5.37 (m, 2 H), 5.18 (t, J=7.0 Hz, 1H) 5.05-4.95 (m, 3 H), 4.34 (dd, J=6.2, 3.4 Hz, 1 H), 3.78 (dd, J=6.8, 2.4 Hz, 1 H), 3.06 (p, J=6.8 Hz, 1 H), 2.75 (br, 2 H), 2.60 (dd, J=16.8, 3.2 Hz, 1 H), 2.46 (t, J=6.4 Hz, 2 H), 2.30 (dd, J=16.8, 6.0 Hz, 1 H), 2.13 (s, 3 H), 2.08-2.03 (m, 1 H), 1.68 (d, J=1.2 Hz, 3 H), 1.66 (d, J=6.0 Hz, 3 H), 1.21 (s, 3 H), 1.07 (s, 3 H), 1.02 (d, J=6.8 Hz, 3 H), 0.98 (d, J=6.8 Hz, 3 H). 0.91 (s, 9 H), 0.86 (s, 9 H), 0.09 (s, 3 H), 0.06 (br, 6 H), 0.01 (s, 3 H); $^{13}$C NMR (100 MHz, CDCl$_3$) δ 218.1, 205.4, 172.0, 137.4, 135.5, 132.8, 125.9, 119.2, 115.9, 78.7, 76.6, 74.1, 53.5, 46.1, 42.8, 40.1, 36.6, 29.3, 26.8, 26.4, 26.2, 23.8, 23.7, 20.0, 19.2, 18.7, 18.4, 18.3, 15.2, -3.7, -4.0, -4.5, -4.8; HRMS (ESI TOF) Calcd for C$_{37}$H$_{68}$O$_6$NaSi$_2$ (M$^+$+Na), 687.4447. Found 687.4403.

Example 10

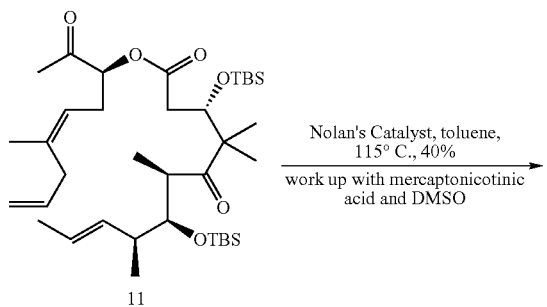

11

-continued

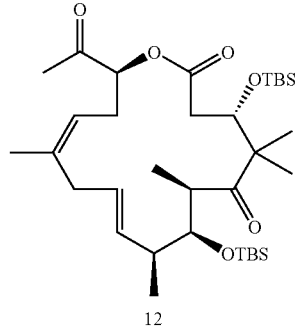

12

The solution of starting material 11 (67 mg, 0.1 mmol, 1.0 equiv.) in toluene (6.0 mL) and the solution of Nolan's catalyst (9.5 mg, 0.01 mmol) in toluene (6.0 mL) was separately added into refluxing toluene (210 mL) in 30 minutes. The resulting reaction mixture was refluxed for 1.5 hours, and mercaptonicotinic acid (4.5 mg, 0.03 mmol) was added. The mixture was stirred for another 10 minutes and cooled in an ice bath for 2 minutes, and then DMSO (0.05 mL) and silica gel (2 gram) were added. After the mixture was stirred at room temperature for 12 hours under air, it was filtered through a pad of silica gel, concentrated; and the residue was purified with column chromatography (0% to 5% of EtOAc in hexanes) to obtain macrolactone 12 (25 mg, 40%) as a white foam; along with recycled starting material 11 (14 mg, 21%). R$_f$=0.60 (hexane/EtOAc, 4:1); [α]$^{20}_D$-28.5° (c 0.8, CHCl$_3$); IR (neat) 2955, 2930, 2886, 2857, 1745, 1731, 1696, 1473, 1464, 1389, 1362, 1252, 1161, 1079, 985, 835, 775 cm$^{-1}$; $^1$H NMR (400 MHz, CDCl$_3$) δ 5.64-5.58 (m, 1 H), 5.39-5.31 (m, 1 H), 5.16 (t, J=7.8 Hz, 1 H), 4.99 (dd, J=9.2, 2.4 Hz, 1 H), 4.21 (dd, J=8.8, 2.4 Hz, 1 H), 3.94 (dd, J=8.4, 0.8 Hz, 1 H), 3.07 (dd, J=15.0, 4.6 Hz, 1 H), 2.95 (m, 2 H), 2.72 (dd, J=15.0, 2.4 Hz, 1 H), 2.60-2.49 (m, 2 H), 2.44-2.27 (m, 2 H), 2.22 (s, 3 H), 1.68 (s, 3 H), 1.18 (s, 3 H), 1.115 (d, J=6.8 Hz, 3 H), 1.113 (s, 3 H), 1.03 (d, J=7.2 Hz, 3 H), 0.93 (s, 9 H), 0.84 (s, 9 H), 0.100 (s, 3 H), 0.097 (s, 3 H), 0.07 (s, 3 H), 0.05 (s, 3 H); $^{13}$C NMR (100 MHz, CDCl$_3$) δ 215.8, 204.9, 171.4, 140.3, 132.8, 129.5, 118.7, 79.0, 78.3, 75.7, 53.9, 48.6, 41.8, 40.5, 34.9, 29.2, 26.7, 26.5, 26.2, 24.7, 23.6, 23.4, 20.9, 18.8, 18.6, 17.7, -3.6 (br), -4.1, -4.8; HRMS (ESI TOF) Calcd for C$_{34}$H$_{63}$O$_6$Si$_2$ (M$^+$+H), 623.4158. Found 623.4128.

Example 11

(R,Z)-3-hydroxy-6-methylnona-5,8-dien-2-one

The title compound was prepared according to the procedure of Rivkin et al., J. Am. Chem. Soc. 126: 10913-10922 (2004).

Example 12

(R,Z)-3-hydroxy-6-(trifluoromethyl)nona-5,8-dien-2-one

The title compound was prepared according to the procedure of Rivkin et al., J. Am. Chem. Soc. 126: 10913-10922 (2004).

Example 13

2-Methyl-3-pentenoic acid

A 1.0 M solution of lithium bis(trimethylsilyl)amide in tetrahydrofuran (THF, 24.5 mL) in 80 mL of freshly distilled THF was cooled to 0° C. and treated with a solution of 3-pentenoic acid (1.0 mL) in 5 mL of THF dropwise over a period of 10 minutes. After stirring for an additional 90 min at 0° C., methyl iodide (1.84 mL) was added and the mixture was allowed to warm to ambient temperature and kept for an additional 1 h. The reaction was quenched by addition of water/THF (1:1 v/v), acidified with 1 N HCl, and extracted with ether. The extract was washed sequentially with 1 N HCl, water, sat. aq. sodium thiosulfate, and brine, then dried over $MgSO_4$, filtered, and concentrated to provide 0.96 g of product. $^1$H-NMR (400 MHz, $CDCl_3$): δ 5.56 (2H, m), 3.10 (1H, dq), 1.69 (3H, dd), 1.26 (3H, d).

Example 14

2-methyl-3-pentenoate N-acetylcysteamine thioester 2-methyl-3-pentenoic acid (575 mg) was dried by concentration twice from benzene, then dissolved in 16 mL of dichloromethane. Thionyl chloride (1.1 mL) was added and the mixture was heated at 43° C. for 30 min. The mixture was evaporated to provide the crude acid chloride. The acid chloride was dissolved in 2.5 mL of benzene and cooled to 15-20° C., and a solution of N-acetylcysteamine (0.54 mL) and pyridine (0.52 mL) in dichloromethane (55 mL) was added dropwise. After 30 min, an additional portion of N-acetylcysteamine (0.54 mL) was added. After an additional 10 min, the mixture as diluted with dichloromethane and washed twice with 1 N HCl, water, and brine, then dried over $MgSO_4$, filtered, and evaporated. The crude product was chromatographed on silica gel (152 g) topped with $CuSO_4$-impregnated silica gel (27 g) using 60% ethyl acetate/hexanes to provide the purified thioester. $^{13}$C-NMR (100 MHz, $CDCl_3$): δ 206, 170.2, 129.2, 128.8, 51.8, 39.6, 28.3, 23.1, 17.9, 17.5.

Example 15

This example provides a chemical synthesis for a compound of formula (II') useful as a starting material for methods of the present invention. The letter identification of the compounds in this example are for the compounds provided in the schemes of FIGS. 6 and 7. The starting material A is described in Smith et al., "Gram-scale synthesis of (+)-discodermolide," *Org. Lett.* (1999) 1: 1823-1826.
Step 1. Preparation of Intermediate B
N-propionyl-(R)-4-benzyloxazolidinone (6.12 g, 26.27 mmol) was placed into a clean and dry round bottom flask under argon atmosphere, dry dichloromethane (100 ml) was added, and the mixture was cooled to −5° C. (internal). Titanium tetrachloride (3.05 ml, 27.85 mmol) was added slowly at −5° C. Stirred for 15 min at the same temperature and then added (−) spartine (18.58 ml, 59.11 mmol), stirred for 15 min at −5° C., then cooled in a −78° C. bath (internal temperature −65° C.). A solution of aldehyde intermediate A (10 g, 26.27 mmol) in dichloromethane (50 ml) was added and stirred at the same temperature for 30 min., then slowly raised the temperature to −20° C. over a period of 30 min. Checked TLC reaction completed, cooled the reaction mixture to −50° C. and added ice cold 1.5 N HCl (100 ml) slowly, extracted with dichloromethane 100 ml×3. The combined extracts were washed sequentially with 1.5 N HCl (100 ml), water (100 ml), 10% sodium bicarbonate solution (100 ml), and saturated brine solution (100 ml), and dried over sodium sulfate. The organic phase was filtered and concentrated to get 20 g of crude viscous liquid that was then purified by column chromatography using silica gel (60-120 mesh). The product eluted at 8% of ethyl acetate in hexane. Collected 10 g of intermediate B as a viscous liquid (62% yield).
Step 2. Preparation of C
Intermediate B (23 g, 37.46 mmol) in dry dichloromethane (230 ml) was added to a clean and dry round bottom flask under nitrogen atmosphere, then cooled to −78° C. Added 2,6-lutidine (10.7 ml, 93.62 mmol), and stirred for 15 min. Added tert-butyldimethylsilyl triflate (12.9 ml, 56.18 mmol) slowly at −78° C., stirred at the same temperature for 1 h. Checked TLC reaction completed. Added 10% sodium bisulfate solution (150 ml), extracted the product 3× using 150 mL of dichloromethane. The extracts were combined and washed with sodium bisulphate solution (100 ml) then with water (250 ml), brine solution (250 ml), dried over sodium sulphate, filtered and concentrated the filtrate to get 30 g of crude material. Purified by column chromatography on silica gel (60-120 mesh). The product eluted at 3% of ethyl acetate in hexane to give 19.2 g (70% yields) of intermediate C as a viscous liquid.
Step 3. Preparation of D
Intermediate C (2 g, 2.749 mmol) was placed into a clean round bottom flask, dissolved in ethyl acetate (20 ml), and the solution was bubbled with nitrogen for 5 min. Then 10% Pd on carbon (200 mg) was added, the mixture was purged with nitrogen then with hydrogen, and stirred under hydrogen atmosphere for 3 h. Filtered the reaction mixture carefully on bed of diatomaceous earth, which was washed with ethylacetate, The filtrate was concentrated and dried azeotropically with toluene to give 2 g of material D as viscous liquid.
Step 4. Preparation of E
To a tetrahydrofuran (14 mL)-water (14 mL) solution containing compound D (1.2 g, 1.98 mmol) and lithium hydroxide monohydrate (135 mg, 3.29 mmol) was added hydrogen peroxide (0.58 mL, 30% solution) dropwise at 0° C. The reaction mixture was stirred for 3 hours at 0° C. to 25° C. Most volatiles were removed under reduced pressure. The residue was diluted with water (100 mL), and extracted with diethyl ether (100 mL, 1×). The aqueous was acidified with sodium bisulfate to pH 2, and was extracted with diethyl ether (100 mL, 2×). All organic extracts were combined, dried over sodium sulfate Column chromatograph (hexanes:acetone/3:1, 1% acetic acid) on silica gel afforded E as an oil (0.96 g).
Step 5. Preparation of F
To a dimethylformamide solution of compound E (0.96 g, 2.1 mmol) and trimethylsilylimidazole (0.46 ml, 3.1 mmol) was added chlorotrimethylsilane (0.4 ml, 3.1 mmol) at ambient temperature. The resulting mixture was stirred at ambient temperature for 1 hour. Diethyl ether (200 ml) was added, and the solution was washed with saturated sodium bisulfate (100 ml, 1×), water (100 ml, 5×), brine (100 ml, 1×) and dried over magnesium sulfate. Quick chromatography on silica gel (hexanes:ethyl acetate/3:1) afforded crude product F (0.9 g)
Step 6. Preparation of G
A mixture of crude compound F (0.96 g, 2.1 mmol) and di-t-butoxy-N,N-dimethylmethanamine (3.5 ml, 20 mmol) was refluxed in benzene (15 ml) for 2 hours. Saturated sodium bisulfate solution (50 ml) was then added, and stirred over 2 hours. Diethyl ether (200 ml) was added, separated, washed with water (100 ml, 1×), saturated sodium bicarbonate (100 ml, 1×), water (100 ml, 1×), brine (100 ml, 1×) and dried over magnesium sulfate. Column chromatography on silica gel (hexanes:ethyl acetate/7:1) afforded product G (0.37 g, 37% yield).
Step 7. Preparation of Compound H:
To a dichloromethane (1.5 mL) solution containing methyl sulfoxide (DMSO) (64 μL, 0.9 mmol) was added oxalyl chloride (38 μL, 0.43 mmol) dropwise at −50° C. The reaction mixture was kept at −50° C. to −20° C. over 10 min. The alcohol G (180 mg, 0.36 mmol) in dichloromethane (1.5 mL) was then introduced. After the reaction mixture was kept at −50° C. to −20° C. over 30 min., triethylamine (0.25 mL, 1.8 mmol) was added. The reaction temperature was allowed to slowly warm to 10° C. in 3 h. It was then diluted with diethyl ether (100 mL), washed with saturated sodium bicarbonate (50 mL, 2×), brine (50 mL, 1×), and dried over magnesium sulfate. Column chromatography on silica gel (hexanes:ethyl acetate/7:1) afforded aldehyde H (140 mg, 78% yield).

Step 8. Preparation of Compound J:

To a THF (1.5 mL) solution containing ethylphenylsulfone (172 mg, 1 mmol) was added n-butyl lithium solution (0.32 mL of 2.5 M solution in hexanes) dropwise at −78° C. After 10 min stirring, the solution was transferred by cannula to a THF (1.5 mL) solution of the aldehyde H (180 mg, 0.36 mmol) at −78° C. After additional 5 min stirring at −78° C., freshly distilled acetic anhydride (0.32 mL, 3.3 mmol) was added by syringe. The reaction temperature was then allowed to slowly warm to ambient temperature over 2 h. It was then quenched with saturated ammonium chloride, extracted with diethyl ether (100 mL, 2×), washed with water (100 mL, 3×), brine (100 mL, 1×), and dried over magnesium sulfate. Column chromatography (hexanes:ethyl acetate/7:1) on silica gel afforded J (220 mg, 83% yield) as a mixture.

Step 9. Preparation of Compound K:

To a methanol (1 mL) and THF (1 mL) solution containing the sulfone J (~0.3 mmol) was added sodium amalgam (0.56 g of 5%, 1.2 mmol) at −20° C. The reaction mixture was stirred at −10° C. to −20° C. over 1 h. Additional sodium amalgam was added, and stirred at −10° C. to 0° C. over 2 h. It was then quenched with saturated ammonium chloride and saturated sodium bisulfate, extracted with diethyl ether (50 mL, 2×), washed with brine (50 mL, 1×), and dried over magnesium sulfate. Column chromatography (hexanes:ethyl acetate/10:1) on silica gel afforded olefin K (100 mg, 54% yield).

Step 10. Preparation of Compound L:

To a dichloromethane (1 mL) solution containing the olefin K (97 mg, 0.19 mmol), and triethylsilane (0.2 mL) was added trifluoroacetic acid (1 mL) dropwise at ambient temperature. The reaction mixture was stirred at ambient temperature for 2 h. The volatiles were removed in vacuo, and the residue was chromatographed on silica gel (hexanes:ethyl acetate/3:1) to afforded the hydroxyl lactone L as a 4:1 mixture of trans/cis isomers (25 mg, 62% yield) along with mono-silylated product (27 mg).

Preparation of Epothilone Intermediate (II):

To a dichloromethane (0.5 mL) solution containing the hydroxyl lactone L (12 mg, 0.057 mmol) was added Dess-Martin periodinane (48 mg, 0.12 mmol) at ambient temperature. The reaction mixture was stirred at ambient temperature for 1 h. Additional Dess-Martin periodinane (48 mg, 0.12 mmol) was added, and stirred over another hour. The reaction was quenched with sodium thiosulfate, extracted with ethyl acetate, washed with water, brine, and dried over magnesium sulfate. Column chromatograph (hexanes:ethyl acetate/3:1) on silica gel, followed by preparative TLC (hexanes:ethyl acetate/3:1, then 2:1) afforded the keto-lactone product 11 (3.5 mg, 29% yield) as a 4:1 mixture of trans/cis isomers.

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A method for preparing an aldehyde compound having the formula:

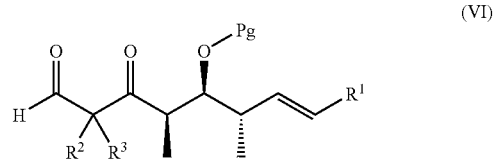

(VI)

wherein $R^1$ is selected from the group consisting of H, unsubstituted lower alkyl and substituted lower alkyl; $R^2$ is selected from the group consisting of unsubstituted lower alkyl and substituted lower alkyl; $R^3$ is selected from the group consisting of H, unsubstituted lower alkyl and substituted lower alkyl; and Pg is a hydroxy protecting group; said method comprising:

(a) contacting a compound of the formula:

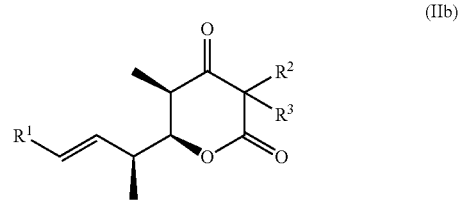

(IIb)

with a reducing agent under conditions sufficient to form a reduced product having the formula

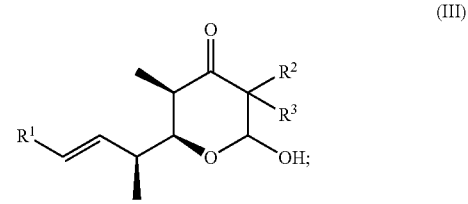

(III)

(b) contacting said reduced product with a mercaptan reagent and a catalyst under conditions sufficient to form a dithioacetal compound having the formula

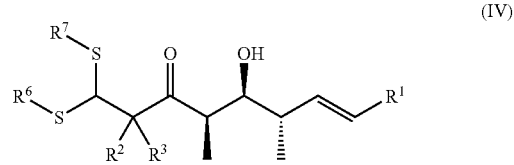

(IV)

wherein each of $R^6$ and $R^7$ is independently selected from the group consisting of $C_1$-$C_{10}$ alkyl, phenyl and benzyl, or $R^6$ and $R^7$ are optionally combined to form a dithiolane or dithiane ring;

(c) contacting said dithioacetal compound with a hydroxyl protecting group reagent under conditions to form a protected compound having the formula

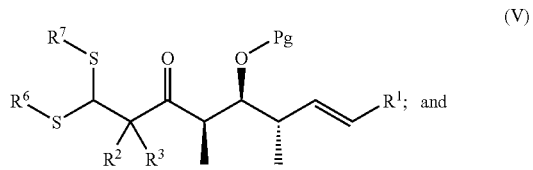

(V)

(d) converting said protected compound to said aldehyde compound.

2. The method of claim 1, wherein Pg is selected from the group consisting of t-butyldimethylsilyl, trimethylsilyl and triethylsilyl.

3. The method of claim 1, wherein said reducing agent is diisobutylaluminum hydride.

4. The method of claim 1, wherein said catalyst is boron trifluoride etherate.

5. The method of claim 1, wherein said mercaptan reagent is selected from the group consisting of 1,2-ethanedithiol, 1,3-propanedithiol, methyl mercaptan, ethyl mercaptan, propyl mercaptan, butyl mercaptan, pentyl mercaptan, benzyl mercaptan and phenyl mercaptan.

6. The method of claim 1, wherein step (d) comprises removing the dithioacetal with bis[(trifluoroacetoxy)]iodobenzene.

7. The method of any of claims 1 to 6, wherein each of $R^1$, $R^2$ and $R^3$ is methyl.

8. A method for the preparation of a compound of formula (VII), said method comprising:

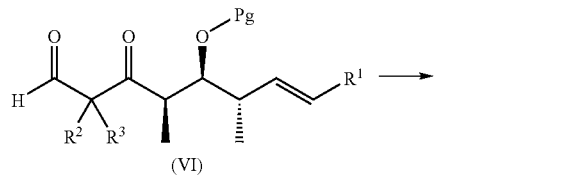

(VI)

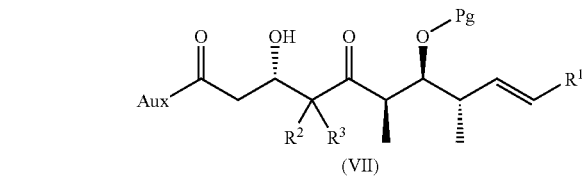

(VII)

(a) contacting a compound of formula (VI) with a chiral aldol reagent under conditions sufficient to produce said compound of formula (VII), wherein Pg is a hydroxy protecting group; $R^1$ is a member selected from the group consisting of H, unsubstituted lower alkyl and substituted lower alkyl; $R^2$ is selected from the group consisting of unsubstituted lower alkyl and substituted lower alkyl; $R^3$ is selected from the group consisting of H, unsubstituted lower alkyl and substituted lower alkyl; and Aux is a chiral auxiliary which produces a diastereomeric ratio of at least 7 to 1 in favor of an S-configuration at the carbon bearing the hydroxy group.

9. The method of claim 8, wherein Aux is N-(2R)-bornane-10,2-sultam.

10. The method of claim 8, wherein Pg is t-butyldimethylsilyl; $R^1$ is methyl, and Aux is N-(2R)-bornane-10,2-sultam.

11. The method of any of claims 8 to 10, wherein each of $R^2$ and $R^3$ is methyl.

12. A method for the preparation of a compound of formula (IX) from a compound of formula (VII),

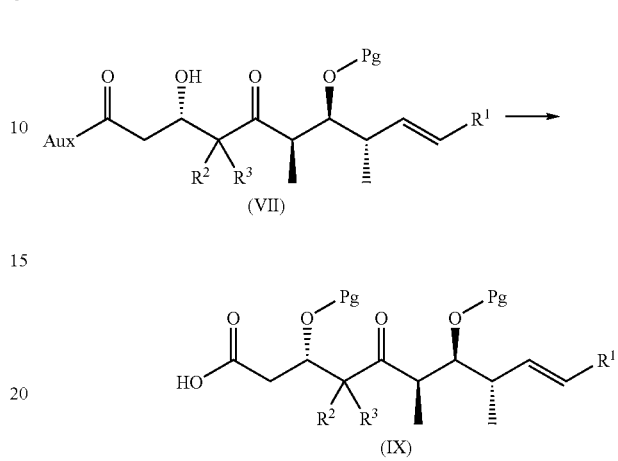

wherein each Pg is an independently selected hydroxy protecting group; $R^1$ is a member selected from the group consisting of H, unsubstituted lower alkyl and substituted lower alkyl; $R^2$ is selected from the group consisting of unsubstituted lower alkyl and substituted lower alkyl; $R^3$ is selected from the group consisting of H, unsubstituted lower alkyl and substituted lower alkyl; and Aux is a chiral auxiliary;

said method comprising:

(a) contacting said compound of formula (VII) with a hydroxy protecting group reagent to attach a protecting group to the hydroxy group; and (b) hydrolyzing said Aux group to produce said compound of formula (IX).

13. The method of claim 12, wherein each Pg is t-butyldimethylsilyl.

14. The method of claim 12, wherein each Pg is t-butyldimethylsilyl; $R^1$ is methyl, and Aux is N-(2R)-bornane-10,2-sultam.

15. The method of any of claims 12 to 14, wherein each of $R^2$ and $R^3$ are methyl.

16. A compound having the formula:

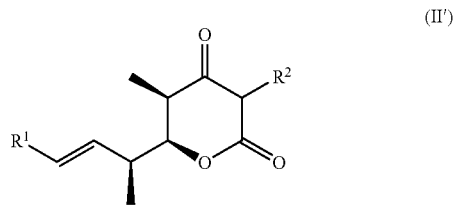

(II')

wherein $R^1$ is selected from the group consisting of H, unsubstituted lower alkyl and substituted lower alkyl; and $R^2$ is selected from the group consisting of unsubstituted lower alkyl and substituted lower alkyl.

17. A compound of claim 16, wherein $R^1$ is methyl and $R^2$ is methyl.

18. A compound having the formula:

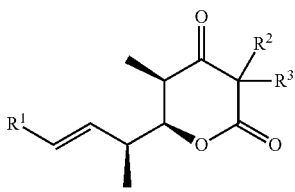
(II)

wherein $R^1$ is selected from the group consisting of H, unsubstituted lower alkyl and substituted lower alkyl; $R^2$ and $R^3$ are each independently selected from the group consisting of unsubstituted lower alkyl and substituted lower alkyl.

19. A compound of claim 18, wherein each of $R^1$, $R^2$ and $R^3$ is methyl.

20. A compound having the formula:

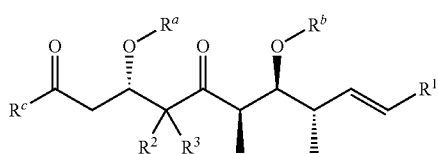
(IX')

wherein $R^a$ and $R^b$ are each independently members selected from the group consisting of H and a hydroxy protecting group; and $R^c$ is a member selected from the group consisting of OH and Aux, wherein Aux represents a chiral auxiliary;

$R^1$ is a member selected from the group consisting of H, unsubstituted lower alkyl and substituted lower alkyl;

$R^2$ is selected from the group consisting of unsubstituted lower alkyl and substituted lower alkyl; and $R^3$ is selected from the group consisting of H, unsubstituted lower alkyl and substituted lower alkyl;

with the proviso that when $R^1$ is OH, $R^b$ is t-butyldimethylsilyl and $R^c$ is H, then $R^a$ is other than triethylsilyl.

21. A compound of claim 20, wherein $R^c$ is OH, $R^a$ and $R^b$ are each t-butyldimethylsilyl and $R^1$ is methyl.

22. A compound of claim 20, wherein $R^c$ is Aux, $R^a$ is H, $R^b$ is t-butyldimethylsilyl and $R^1$ is methyl.

23. A compound of claim 20, wherein $R^c$ is Aux, $R^a$ and $R^b$ are each t-butyldimethylsilyl and $R^1$ is methyl.

* * * * *